(12) United States Patent
Ananthan et al.

(10) Patent No.: US 7,541,364 B2
(45) Date of Patent: Jun. 2, 2009

(54) PYRIDOMORPHINANS, PYRIDAZINOMORPHINANS AND USE THEREOF

(75) Inventors: Subramaniam Ananthan, Birmingham, AL (US); Richard B. Rothman, Baltimore, MD (US); Edward J. Bilsky, Biddeford, ME (US); Frank Porreca, Tucson, AZ (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 11/718,565

(22) PCT Filed: Aug. 27, 2004

(86) PCT No.: PCT/US2004/027802

§ 371 (c)(1),
(2), (4) Date: Mar. 18, 2008

(87) PCT Pub. No.: WO2005/020914

PCT Pub. Date: Mar. 10, 2005

(65) Prior Publication Data

US 2008/0194568 A1    Aug. 14, 2008

Related U.S. Application Data

(60) Provisional application No. 60/497,901, filed on Aug. 27, 2003.

(51) Int. Cl.
*A61K 31/4748* (2006.01)
*C07D 491/12* (2006.01)

(52) U.S. Cl. .......................... 514/279; 546/40; 544/233; 514/248

(58) Field of Classification Search .............. 514/279, 514/248; 546/40; 544/233
See application file for complete search history.

(56) References Cited

U.S. PATENT DOCUMENTS

| | | | |
|---|---|---|---|
| 6,465,479 B1 | 10/2002 | Ananthan | |
| 7,015,326 B1 | 3/2006 | Ananthan | |
| 7,105,675 B2 | 9/2006 | Ananthan | |
| 2006/0264452 A1 | 11/2006 | Ananthan | |

FOREIGN PATENT DOCUMENTS

WO    WO 2006130471    12/2006

OTHER PUBLICATIONS

Ullrich, T. et al.: derivatives of the 17-(2-methylallyl)-substituted noroxymorphone: Variation of the delta address and its effects on affinity and selectivity for the delta opioid receptor. Bioorg. & med. Chem. Lett., vol. 11, pp. 2883-2885, 2001.*

"Synthesis, Opioid Receptor Binding, and Bioassay of Naltrindole Analogues Substituted in the Indolic Benzene Moiety"; Subramaniam Ananthan et al.; J. Med. Chem. 1998, 41, 2872-2881.
"Synthesis, Opioid Receptor Binding, and Biological Activities of Naltrexone-Derived Pyrido- and Pyrimidomorphinans"; Subramaniam Ananthan et al.; J. Med. Chem. 1999, 42, 3527-3538.
"Synthesis, Opioid Receptor Binding, and Functional Activity of 5'-Substituted 17-Cyclopropylmethylpyrido[2',3':6,7]morphinans"; Subramaniam Ananthan et al.; Science Direct, Bioorganic & Medicinal Chemistry Letters 13 (2003) 529-532.
"Novel Ligands for the Opioid Receptors: Synthesis and Structure-Activity Relationships among 5'-Aryl and 5'Heteroaryl 17-Cyclopropylmethyl-4,5 α-epoxypyrido[2',3':6,7]morphinans"; Subramaniam Ananthan et al.; Science Direct, Bioorganic & Medicinal Chemistry 11 (2003) 4143-4154.
"Identification of Opioid Ligands Processing Mixed μ Agonist/δ Antagonist Activity among Pyridomorphinans Derived from Naloxone, Oxymorphone, and Hydromorphone"; Subramaniam Ananthan et al.; J. Med. Chem. 2004, 47, 1400-1412.
Calcagnetti, D. J.; Keck, B. J.; Quatrella, L. A.; Schechter, M. D. Blockade of cocaine-induced conditioned place preference; relevance to cocaine abuse therapeutics. *Life sciences* 1995, 56, 475-483.
Coop, A.; Rice, K. C. Role of delta-opioid receptors in biological processes. *Drug news & perspectives* 2000, 13, 481-487.
Heidbreder, C.; Goldberg, S. R.; Shippenberg, T. S. Inhibition of cocaine-induced sensitization by the delta-opiod receptor antagonist naltrindole. *European journal of pharmacology* 1993, 243, 123-127.
Heidbreder, C.; Shoaib, M.; Shippenberg, T. S. Differential role of delta-opioid receptors in the development and expression of behavioral sensitization to cocaine. *European journal of pharmacology* 1996, 298, 207-216.

(Continued)

*Primary Examiner*—Charanjit S Aulakh
(74) *Attorney, Agent, or Firm*—Connolly Bove Lodge & Hutz LLP; Burton A. Amernick

(57) ABSTRACT

Compounds represented by the formula:

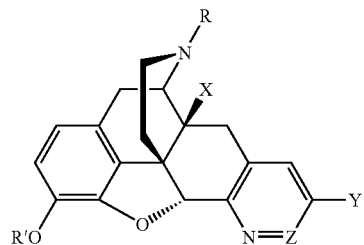

wherein R is $C_{1-6}$ alkyl; $C_{4-6}$ cycloalkylalkyl; or $C_{3-6}$ alkenyl; R' is H or $C_{1-6}$ alkyl; X is H or OH; Y is alkyl, cycloalkyl, aryl, heteroaryl, arylalkyl or aroyl; and Z is CH or N; provided that X is H, when Z is CH and R is $C_4$ cycloalkylalkyl or $C_4$ alkenyl; prodrugs thereof; and pharmaceutically acceptable salts thereof are provided. Compounds of the above formula are useful as analgesics for treating pain; as immunomodulators, to modulate the behavioral effects of drugs of abuse and to modulate the development of tolerance and dependence to μ agonists.

19 Claims, 4 Drawing Sheets

OTHER PUBLICATIONS

Menkens, K.; Bilsky, E. J.; Wild, K. D.; Portoghese, P. S.; Reid, L. D.; Porreca, F. Cocaine place preference is blocked by the delta-opioid receptor antagonist, naltrindole. *European journal of pharmacology* 1992, 219, 345-346.

Reid, L.D.; Glick, S. D.; Menkens, K. A.; French, E. D.; Bilsky, E. J.; Porreca, F. Cocaine self-administration and naltrindole, a delta-selective opioid antagonist. *Neuroreport* 1995, 6, 1409-1412.

Reid, L.D.; Hubbell, C. L.; Glaccum, M. B.; Bilsky, E. J.; Portoghese, P. S.; Porreca, F. Naltrindole, an opioid delta receptor antagonist, blocks cocaine-induced facilitation of responding for rewarding brain stimulation. *Life sciences* 1993, 52, PL67-71.

Shippenberg, T. S.; Heidbreder, C. The delta-opioid receptor antagonist naltrindole prevents sensitization to the conditioned rewarding effects of cocaine. *European journal of pharmacology* 1995, 280, 55-61.

Suzuki, T.; Mori, T.; Funada, M.; Misawa, M.; Nagase, H. Attenuation of the discriminative stimulus properties of cocaine by delta-opioid receptor antagonists. *European journal of pharmacology* 1994, 263, 207-211.

Suzuki, T.; Mori, T.; Tsuji, M.; Misawa, M.; Nagase, H. The role of delta-opioid receptor subtypes in cocaine- and methamphetamine-induced place preferences. *Life sciences* 1994, 55, PL339-344.

Froehlich, J. C.; Badia-Elder, N. E.; Zink, R. W.; McCullough, D. E.; Portoghese, P. S. Contribution of the opioid system to alcohol aversion and alcohol drinking behavior. *The Journal of pharmacology and experimental therapeutics* 1998, 287, 284-292.

Krishnan-Sarin, S.; Jing, S. L.; Kurtz, D. L.; Zweifel, M.; Portoghese, P.S.; Li, T. K.; Froehlich, J. C. The delta opioid receptor antagonist naltrindole attenuates both alcohol and saccharin intake in rats selectively bred for alcohol preference. *Psychopharmacology* 1995, 120, 177-185.

Krishnan-Sarin, S.; Portoghese, P.S.; Li, T. K.; Froehlich, J. C. The delta 2-opioid receptor antagonist naltriben selectively attenuates alcohol intake in rats bred for alcohol preference. *Pharmacology, biochemistry, and behavior* 1995, 52, 153-159.

June, H. L.; McCane, S. R.; Zink, R. W.; Portoghese, P. S.; Li, T. K.; Froehlich, J. C. The delta 2-opioid receptor antagonist naltriben reduces motivated responding for ethanol. *Psychopharmacology* 1999, 147, 81-89.

Abdelhamid, E. E.; Sultana, M.; Portoghese, P. S.; Takemori, A. E. Selective blockage of delta opioid receptors prevents the development of morphine tolerance and dependence in mice. *The Journal of pharmacology and experimental therapeutics* 1991, 258, 299-303.

Hepburn, M. J.; Little, P. J.; Gingras, J.; Kuhn, C. M. Differential effects of naltrindole on morphine-induced tolerance and physical dependence in rats. *The Journal of pharmacology and experimental therapeutics* 1997, 281, 1350-1356.

Suzuki, T.; Tsuji, M.; Mori, T.; Misawa, M.; Nagase, H. Involvement of delta 1 and delta 2 opioid receptor subtypes in the development of phsyical dependence on morphine in mice. *Pharmacology, biochemistry, and behavior* 1997, 57, 293-299.

Arakawa, K.; Akami, T.; Okamoto, M.; Akioka, K.; Nakai, I.; Oka, T.; Nagase, H. Immunosuppression by delta opioid receptor antagonist. *Transplantation proceedings* 1993, 25, 738-740.

Arakawa, K.; Akami, T.; Okamoto, M.; Oka, T.; Nagase, H.; Matsumoto, S. The immunosuppressive effect of delta-opioid receptor antagonist on rat renal allograft survival. *Transplantation* 1992, 53, 951-953.

Carr, D. J.; Radulescu, R. T.; deCosta, B. R.; Rice, K. C.; Blalock, J. E. Differential effect of opioids on immunoglobulin production by lymphocytes isolated from Peyer's patches and spleen. *Life sciences* 1990, 47, 1059-1069.

House, R. V.; Thomas, P. T.; Kozak, J. T.; Bhargava, H. N. Suppression of immune function by non-peptidic delta opioid receptor antagonists. *Neuroscience letters* 1995, 198, 119-122.

Linner, K. M.; Stickney, B. J.; Quist, H. E.; Sharp, B. M.; Portoghese, P. S. The delta1-opioid receptor antagonist, 7-(benzospiroindanyl)naltrexone [correction of 7-benzylspiroindanylnaltrexone], prolongs renal allograft survival in a rat model. *European journal of pharmacology* 1998, 354, R3-5.

\* cited by examiner

PYRIDOMORPHINANS, PYRIDAZINOMORPHINANS AND USE THEREOF

FEDERALLY SPONSORED RESEARCH OR DEVELOPMENT

This invention was made using funds under Grant DA 08883 from the National Institute on Drug Abuse and the US Government has certain rights in the invention.

TECHNICAL FIELD

The present invention relates to certain pyridomorphianan and pyridazinomorphinan compounds and more particularly to pyridomorphianan and pyridazinomorphinan derivatives of oxymorphone, hydromorphone, oxycodone, hydrocodone, naloxone, and naltrexone. Compounds of the present invention exhibit antagonist or partial agonist activity at the opioid δ receptor. Moreover, various compounds of the present invention possess μ agonist characteristics.

Compounds of the present invention are especially useful for treating patients suffering from pain. Compounds of the present invention are also suitable for treating patients suffering from drug of abuse such as cocaine, amphetamines, heroin and other opioid drugs. Compounds of the present invention are also useful for treatment of alcoholism and for treatment of patients suffering from autism and Tourette's syndrome. Compounds of the present invention may also be used as cough suppressants and as immunomodulatory agents and for prevention of organ rejection in organ transplant patients.

BACKGROUND OF THE INVENTION

Chronic pain represents a major health and economic problem throughout the world. Despite major advances in understanding the physiological and pathological basis of pain, and ideal analgesic is yet to be discovered. Among analgesic drugs, the opioid class of compounds still remain the effective treatment agents for severe and chronic pain. For instance, see Parrot, Using Opioid Analgesic to Manage Chronic Noncancer Pain in Primary Care, *J. Am. Board Fam. Pract.* 1999, 12, 293-306 and Cherny, New Strategies in Opioid Therapy for Cancer Pain, *J. Oncol. Manage* 2000, 9, 8-15.

The opioid drugs produce their biological effects through their interaction with opioid receptors, which belong to the family of seven transmembrane G-protein coupled receptors. The existence of three opioid receptor types μ, δ and κ has been clearly established and is confirmed by cloning of these three receptors from mouse, rat, and human cDNAs. Along these lines, see Dhawan et al. International Union of Pharmacology. XII. Classification of Opioid Receptors, *Pharmacol. Rev.* 1996, 48, 567-592; and Aldrich, Analgesics, In *Burger's Medicinal Chemisty and Drug Discovery*, 5$^{th}$ ed.; Wolff, M. E., Ed.; John Wiley & Sons: New York, 1996; Vol. 3. Therapeutic Agents; pp 321-441.

All three opioid receptor types are located in the human central nervous system and each has a role in the mediation of pain. Morphine and related opioids currently prescribed as potent analgesics for the treatment of pain produce their analgesic activity primarily through their agonist action at the μ opioid receptors. The general administration of these medications is limited by significant side effects such as respiratory depression, muscle rigidity, emesis, constipation, tolerance, and physical dependence. For example, see Duthie, Adverse Effects of Opioid Analgesic Drugs, *Br. J. Anaesth.* 1987, 59, 61-77 and van Ree et al., Opioids, Reward and Addiction: An Encounter of Biology, Psychology, and Medicine. *Pharmacol. Rev.* 1999, 51, 341-396.

A large body of evidence indicates the existence of physical or functional interactions between μ and δ receptors. Ligands with agonist or antagonist action at the δ receptor, for example, have been shown to modulate the analgesic and adverse effects of μ agonists. See, for instance, Traynor et al., δ-Opioid Receptor Subtypes and Cross-talk with μ-receptors. *Trends Pharmacol. Sci.* 1993, 14, 84-86; Rothman et al., Allosteric Coupling Among Opioid Receptors: Evidence for an Opioid Receptor Complex, In *Handbook of Experimental Pharmacology, Volume 104, Opioid I*; Hertz et al., Eds; Springer-Verlag: Berlin, 1993; pp 217-237; Jordan et al., G-Protein-Coupled Receptor Heterodimerization Modulates Receptor Function. *Nature* 1999, 399, 697-700; George et al., Oligomerization of μ- and δ-Opioid Receptors, *J. Biol. Chem.* 2000, 275, 26128-26135; Levac et al., Oligomerization of Opioid Receptors: Generation of Novel Signaling Units, *Curr. Opin. Pharmacol.*, 2002, 2, 76-81.

On the other hand, agonist action at the δ receptors potentiate μ mediated analgesic effects, antagonist action at the δ receptor suppresses the tolerance, physical dependence, and related side effects of μ agonists without affecting their analgesic activity. In a study using the nonpeptide ligand naltrindole, Abdelhamid et al. demonstrated that the δ receptor antagonist greatly reduced the development of morphine tolerance and dependence in mice in both the acute and chronic models without affecting the analgesic actions of morphine. See Abdelhamid et al., Selective Blockage of Delta Opioid Receptors Prevents the Development of Morphine Tolerance and Dependence in Mice. *J. Pharmacol. Exp. Ther.* 1991, 258, 299-303.

Fundytus et al., reported that continuous infusion of the δ selective antagonist TIPP[Ψ] by the intracerbroventricular (icv) route in parallel with continuous administration of morphine by the subcutaneous route to rats attenuated the development of morphine tolerance and dependence to a large extent. See Fundytus, et al., Attenuation of Morphine Tolerance and Dependence with the Highly Selective δ-Opioid Receptor Antagonist TIPP[ψ], *Eur. J. Pharmacol.* 1995, 286, 105-108.

Schiller et al., found that the peptide ligand DIPP-NH$_2$[Ψ] displayed mixed μ agonist/δ antagonist properties in vitro and that the compound given icv produced analgesic effect with no physical dependence and less tolerance than morphine in rats. See Schiller et al., Four different types of Opioid Peptides with mixed μ Agonist/δ Antagonist Properties Analgesia 1995, 1, 703-706; and Schiller et al., The Opioid μ Agonist/δ Antagonist DIPP-NH$_2$[ψ] Produces a Potent Analgesic Effect, No Physical Dependence, and Less Tolerance than Morphine in Rats, *J. Med. Chem.* 1999, 42, 3520-3526.

Studies with antisense oligonucleotides of δ receptor have demonstrated that reduction of δ receptor expression diminishes the development and/or expression of morphine dependence without compromising antinociception produced by μ agonists. See Suzuki et al., Antisense Oligodeoxynucleotide to δ Opioid Receptors Attenuates Morphine Dependence in Mice, *Life Sci.* 1997, 61, PL 165-170; and Sanchez-Blazquez et al., Antisense Oligodeoxynucleotides to Opioid Mu and Delta Receptors Reduced Morphine Dependence in Mice: Role of Delta-2 Opioid Receptors, *J. Pharmacol. Exp. Ther.* 1997, 280, 1423-1431. Furthermore, genetic deletion studies using δ receptor knockout mice have shown that these mutant mice retain supraspinal analgesia and do not develop analgesic tolerance to morphine. Zhu et al., Retention of Supraspinal Delta-like Analgesia and Loss of Morphine Tolerance in δ Opioid Receptor Knockout Mice, *Neuron,* 1999, 24, 243-252.

These observations suggest that the development of opioid ligands, especially nonpeptide ligands possessing mixed μ agonist/δ antagonist activity may provide a novel approach for the development of analgesic agents with low propensity to produce tolerance, physical dependence, and other side effects.

In studies on naltrexone-derived heterocycle annulated morphinan ligands, it was found that the pyridomorphinan 2a (chart 1) displayed high affinity binding at the opioid receptors and that the binding affinity and antagonist potency of the pyridomorphinans at the δ receptors are modulated by the substituents placed at the 5'-position on the pyridine moiety. For example, the introduction of aromatic groups such as a phenyl group (2b) (chart 1) or a 1-pyrrolyl group at this position gave ligands with high binding affinity and improved δ antagonist potency as determined in bioassays using mouse vas deferens smooth muscle preparations. See Ananthan et al. (I), Synthesis, Opioid Receptor Binding, and Biological Activities of Naltrexone-Derived Pyrido- and Pyrimidomorphinans, *J. Med. Chem.* 1999, 42, 3527-3538; and Ananthan et al. (II), Synthesis, Opioid Receptor Binding, and Functional Activity of 5'-Substituted 17-Cyclopropylmethylpyrido[2',3':6,7]morphinans. *Bioorg. Med. Chem. Lett.* 2003, 13, 529-532.

Interestingly, among phenyl ring substituted analogues of 2b (chart 1), the p-chlorophenyl compound (2c) (chart 1) displayed a mixed μ agonist/δ antagonist profile of activity in the smooth muscle assays in vitro. See Ananthan et al. (I), supra. In analgesic activity evaluations, this compound displayed partial agonist activity in the tail-flick assay and a full agonist activity in the acetic acid writhing assay after icv or ip administration in mice, and it did not produce tolerance to antinociceptive effects on repeated ip injections. Studies in mice with selective antagonists, characterized this compound as a partial μ agonist/δ antagonist. See Wells et al., In Vivo Pharmacological Characterization of SoRI 9409, a Nonpeptidic Opioid μ-Agonist/δ-Antagonist That Produces Limited Antinociceptive Tolerance and Attenuates Morphine Physical Dependence. *J. Pharmacol. Exp. Ther.* 2001, 297, 597-605.

Paradoxically, however, in the in vitro biochemical assays using [$^{35}$S]GTP-γ-S binding, compound 2c(chart 1) failed to display μ agonist activity in guinea pig caudate membranes as well as in cloned cells expressing human μ receptors. See Xu et al., SoRI-9409, a Non-peptide Opioid μ Receptor Agonist/δ Receptor Antagonist, Fails to Stimulate [$^{35}$S]-GTP-γ-S Binding at Cloned Opioid Receptors. *Brain Res. Bull.* 2001, 55, 507-511.

SUMMARY OF THE INVENTION

The present invention relates to compounds represented by the following formula:

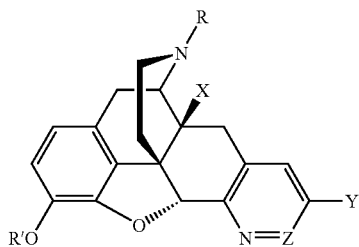

Wherein R is selected from the group consisting of $C_{1-6}$ alkyl; $C_{4-6}$ cycloalkylalkyl; and $C_{3-6}$ alkenyl;

R' is H or $C_{1-6}$ alkyl;

X is H or OH;

Y is selected from the group consisting of alkyl, cycloalkyl, aryl, heteroaryl, arylalkyl and aroyl; and Z is CH or N; provided that X is H when Z is CH and R is $C_4$ cycloalkylalkyl or $C_4$ alkenyl; prodrugs thereof and pharmaceutically acceptable salts thereof.

The present invention also relates to treating a patient suffering from pain which comprises administering to the patient a pain treating effective amount of at least one of the above compounds.

A further aspect of the present invention relates to treating a patient in need of an immunomodulatory agent which comprises administering to the patient an immunomodulatory effective amount of at least one of the above compounds.

A still further aspect of the present invention relates to treating a patient suffering from drug abuse which comprises administering an effective amount for treating drug abuse of at least one of the above compounds.

Another aspect of the present invention is concerned with treating a patient suffering from dependence on or tolerance to a μ agonist which comprises administering to the patient at least one of the above compounds in an amount effective to modulate the tolerance to or dependence on μ agonists, such as morphine.

Still other objects and advantages of the present invention will become readily apparent to those skilled in the art from the following detailed description, wherein it is shown and described preferred embodiments of the invention, simply by way of illustration of the best mode contemplated of carrying out the invention. As will be realized the invention is capable of modifications in various obvious respects, without departing from the invention. Accordingly, the description is to be regarded as illustrative in nature and not as restrictive.

BEST AND VARIOUS MODES FOR CARRYING OUT INVENTION

Figure 1:
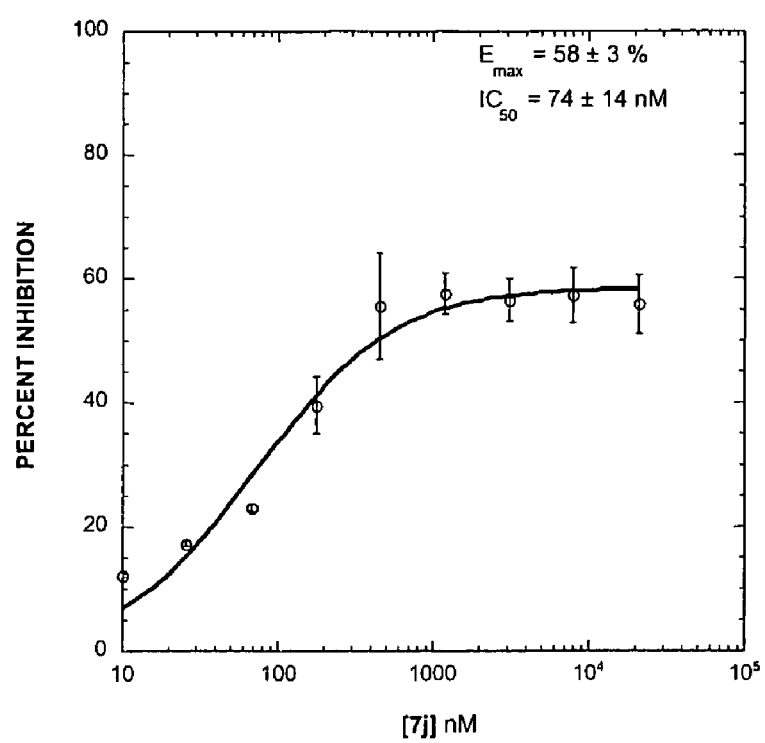
FIG. 1 illustrates a Concentration-response curve for inhibition of SNC-80 stimulated [$^{35}$S]GTP-γ-S binding by 7j (chart 1).

The compounds according to the present invention are represented by the following formula:

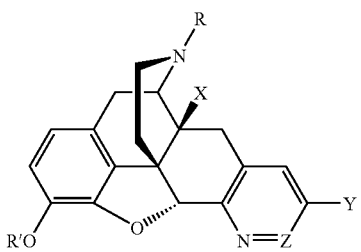

Wherein R is selected from the group consisting of $C_{1-6}$ alkyl; $C_{4-6}$ cycloalkylalkyl; and $C_{3-6}$ alkenyl;

R' is H or $C_{1-6}$ alkyl;

X is H or OH;

Y is selected from the group consisting of alkyl, cycloalkyl, aryl, heteroaryl, arylalkyl and aroyl; and Z is CH or N; provided that X is H when Z is CH and R is $C_4$ cycloalkylalkyl or $C_4$ alkenyl; prodrugs thereof and pharmaceutically acceptable salts thereof. According to certain preferred aspects of the present invention, when Z is CH and R is $C_{4-6}$ cycloalkylalkyl or $C_{3-6}$ alkenyl, then X is H. In addition, Z is more typically CH.

Listed below are definitions of various terms used to describe this invention. These definitions apply to the terms as they are used throughout this specification, unless otherwise limited in specific instances, either individually or as part of a larger group.

The term "aryl" refers to monocyclic or bicyclic aromatic hydrocarbon groups having 6 to 12 carbon atoms in the ring portion, such as phenyl, naphthyl, biphenyl, and diphenyl groups, each of which may be substituted. Some typical substitutions for the aryl group include amino, nitro, halo and alkyl.

The term "alkyl" refers to straight or branched chain unsubstituted hydrocarbon groups of 1 to 20 carbon atoms, more typically 1 to 6 carbon atoms. The expression "lower alkyl" refers to unsubstituted alkyl groups of 1 to 4 carbon atoms.

Examples of suitable alkyl groups include methyl, ethyl and propyl. Examples of branches alkyl groups include isopropyl and t-butyl.

The term "alkenyl" refers to straight or branched chain unsubstituted hydrocarbon groups typically having 3 to 6 carbon atoms.

The term "aralkyl" or "alkylaryl" refers to an aryl group bonded directly through an alkyl group, such as benzyl or phenethyl.

The term "cycloalkyl" refers cyclic hydrocarbon ring systems typically containing 3-9 carbon atoms, with typical examples being cyclopropyl, cyclobutyl, cyclopentyl, cyclohexyl, and cycloheptyl.

The term "cycloalkylalky" refers to alkyl substituted cyclic hydrocarbon ring system wherein the cyclic hydrocarbon typically contains 3-6 carbon atoms, a typical example being cyclopropylalkyl.

The term aroyl refers to C(O)-aryl moieties wherein the aryl portion refers to monocyclic or bicyclic aromatic hydrocarbon groups having 6 to 12 carbon atoms in the ring portion.

The term "heteroaryl", refers to an optionally substituted, unsaturated aromatic cyclic group, for example, which is a 5 or 7 membered monocyclic, 7 to 11 membered bicyclic, or 10 to 15 membered tricyclic ring system, which has at least one heteroatom and at least one carbon atom in the ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized.

Pharmaceutically acceptable salts of the compounds of the present invention include those derived from pharmaceutically acceptable, inorganic and organic acids and bases. Examples of suitable acids include hydrochloric, hydrobromic, sulfuric, nitric, perchloric, fumaric, maleic, phosphoric, glycolic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include alkali such as sodium and ammonium.

Prodrug forms of the compounds bearing various nitrogen functions (amino, hydroxyamino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups as defined earlier.

(a) Carboxamides, —NHC(O)R
(b) Carbamates, —NHC(O)OR
(c) (Acyloxy)alkyl Carbamates, NHC(O)OROC(O)R
(d) Enamines, —NHCR(=CHCO$_2$R) or —NHCR(=CHCONR$_2$)
(e) Schiff Bases, —N=CR$_2$ The preferred compounds of the present invention are those wherein R is CH$_3$ and X is H.

Some specific compounds according to the present invention are the following:

17-(Allyl)-6,7-didehydro-3,14-dihydroxy-4,5α-epoxy-5'-(4-chlorophenyl)pyrido[2',3':6,7]morphinan;

6,7-Didehydro-3,14-dihydroxy-4,5α-epoxy-17-methylpyrido[2',3':6,7]morphinan;

6,7-Didehydro-4,5α-epoxy-14-hydroxy-3-methoxy-17-methylpyrido[2',3':6,7]morphinan;

6,7-Didehydro-3,14-dihydroxy-4,5α-epoxy-17-methyl-5'-phenylpyrido[2',3':6,7]morphinan;

6,7-Didehydro-14-hydroxy-4,5α-epoxy-3-methoxyl-17-methyl-5'-phenylpyrido[2',3':6,7]morphinan;

5'-(4-Chlorophenyl)-6,7-didehydro-3,14-dihydroxy-4,5α-epoxy-17-methylpyrido[2',3':6,7]morphinan;

5'-(4-Chlorophenyl)-6,7-didehydro-14-hydroxy-4,5α-epoxy-3-methoxyl-17-methylpyrido[2',3':6,7]morphinan;

5'-(4-Bromophenyl)-6,7-didehydro-3,14-dihydroxy-4,5α-epoxy-17-methylpyrido[2',3':6,7]morphinan;

5'-(4-Bromophenyl)-6,7-didehydro-3,14-dihydroxy-4,5α-epoxy-3-methoxy-17-methylpyrido[2',3':6,7]morphinan;

6,7-Didehydro-4,5α-epoxy-3-hydroxy-17-methylpyrido[2',3':6,7]morphinan;

6,7-Didehydro-4,5α-epoxy-3-hydroxy-17-methyl-5'-phenylpyrido[2',3':6,7]morphinan;

5'-(4-Chlorophenyl)-6,7-didehydro-4,5α-epoxy-3-hydroxy-17-methylpyrido[2',3':6,7]morphinan;

5'-(4-Bromophenyl)-6,7-didehydro-4,5α-epoxy-3-hydroxy-17-methylpyrido[2',3':6,7]morphinan;

5'-(3,4-Dichlorophenyl)-6,7-didehydro-4,5α-epoxy-3-hydroxy-17-methylpyrido[2',3':6,7]morphinan;

5'-(2,4-Dichlorophenyl)-6,7-didehydro-4,5α-epoxy-3-hydroxy-17-methylpyrido[2',3':6,7]morphinan;

5'-(4-Chlorophenyl)-17-(cyclopropylmethyl)-6,7-didehydro-4,5α-epoxy-3-hydroxypyrido[2',3':6,7]morphinan;

5'-(4-Chlorophenyl)-17-(cyclopropylmethyl)-6,7-didehydro-4,5α-epoxy-3-methoxypyrido[2',3':6,7]morphinan;

5'-(4-Chlorophenyl)-17-[(2-cyclohexyl)ethyl]-6,7-didehydro-4,5α-epoxy-3-methoxypyrido[2',3':6,7]morphinan;
5'-(4-Chlorophenyl)-17-[(2-cyclohexyl)ethyl]-6,7-didehydro-4,5α-epoxy-3-hydroxypyrido[2',3':6,7]morphinan;
5'-(Cyclohexyl)-17-(cyclopropylmethyl)-6,7-didehydro-3,14-dihydroxy-4,5α-epoxypyrido[2',3':6,7]morphinan;
5'-(Cyclohexyl)-6,7-didehydro-4,5α-epoxy-3-hydroxy-17-methylpyrido[2',3':6,7]morphinan;
17-(Allyl)-5'-benzyl-6,7-didehydro-3,14-dihydroxy-4,5α-epoxypyrido[2',3':6,7]morphinan;
5'-Benzyl-17-(cyclopropylmethyl)-6,7-didehydro-3,14-dihydroxy-4,5α-epoxy-pyrido[2',3':6,7]morphinan;
5'-Benzyl-6,7-didehydro-3,14-dihydroxy-4,5α-epoxy-17-methyl-pyrido[2!,3':6,7]morphinan;
17-(Cyclopropylmethyl)-6,7-didehydro-3,14-dihydroxy-4,5α-epoxy-5'-(2-hydroxybenzoyl)pyrido[2',3':6,7]morphinan;
6,7-Didehydro-4,5α-epoxy-3-hydroxy-5'-(2-hydroxybenzoyl)-17-methylpyrido[2',3':6,7]morphinan;
17-(Cyclopropylmethyl)-6,7-didehydro-3,14-dihydroxy-4,5α-epoxy-6'-phenylpyridazino[3',4':6,7]morphinan;
17-(Cyclopropylmethyl)-6,7-didehydro-3,14-dihydroxy-4,5α-epoxy-6'-(4-chlorophenyl)pyridazino[3',4':6,7]morphinan;
6,7-Didehydro-4,5α-epoxy-3-hydroxy-17-methyl-6'-phenylpyridazino[3',4':6,7]morphinan;
6,7-Didehydro-4,5α-epoxy-3-hydroxy-17-methyl-6'-(4-chlorophenyl)pyridazino[3',4':6,7]morphinan;
6,7-Didehydro-4,5α-epoxy-5'-(2-fluorophenyl)-3-hydroxy-17-methylpyrido[2',3':6,7]morphinan;
5'-(2-Chlorophenyl)-6,7-didehydro-4,5α-epoxy-3-hydroxy-17-methylpyrido[2',3':6,7]morphinan;
5'-(2-Bromophenyl)-6,7-didehydro-4,5α-epoxy-3-hydroxy-17-methylpyrido[2',3':6,7]morphinan;
6,7-Didehydro-4,5α-epoxy-3-hydroxy-5'-(2-methylphenyl)-17-methylpyrido[2',3':6,7]morphinan;
6,7-Didehydro-4,5α-epoxy-3-hydroxy-17-methyl-5'-(2-nitrophenyl)pyrido[2',3':6,7]morphinan;
5'-(2-Aminophenyl)-6,7-didehydro-4,5α-epoxy-3-hydroxy-17-methylpyrido[2',3':6,7]morphinan;
6,7-Didehydro-4,5α-epoxy-3-hydroxy-17-methyl-5'-(2-pyridyl)pyrido[2',3':6,7]morphinan; and
6,7-Didehydro-4,5α-epoxy-3-hydroxy-17-methyl-5'-(4-quinolinyl)pyrido[2',3':6,7]morphinan.

Compounds of the present invention can be prepared from commercially available morphinan ketones using the pyridine annulation methodology earlier developed for prior morphinans as disclosed in Ananthan et al. (I), supra; and Ananthan et al. (II), supra and As depicted in Scheme 1 below the condensation of naloxone (4) or hydromorphone (6) with 4-chlorophenylmalondialdehyde (9) in the presence of ammonium acetate in acetic acid gives the corresponding pyridine compounds 7a and 7h, respectively. Since oxymorphone (5) was not commercially available, oxycodone (8) is used as the starting material for the preparation of the target compounds possessing oxymorphone framework. Thus, the condensation of 8 with the aldehyde 9 under the standard reaction conditions gives the methyl ether 7o which is then converted to 7d by phenolic O-demethylation using BBr₃. The target compounds 7f, 7g, and 7i-k are obtained by reacting hydromorphone (6) with the enaminoaldehydes 10-14 and ammonium acetate (Scheme 2). Oxycodone (8) is reacted with the aldehydes 10-12 to obtain the corresponding methyl ethers 7m, 7n, and 7p, which are then demethylated with BBr₃ to yield the target compounds 7b, 7c, and 7e, respectively. The 14-deoxy analogue of 2c is synthesized by the sequence of reactions shown in Scheme 3. Pyridine ring annulation reaction of hydrocodone (15) with the malondialdehyde 9 gives the pyridomorphinan 16, which is then converted to the N-nor compound 17 by reaction with vinyl chloroformate followed by hydrolysis of the resulting carbamate intermediate. Alkylation of 17 with cyclopropylmethyl bromide followed by removal of the methyl group from the ether function gives the desired target compound 7l.

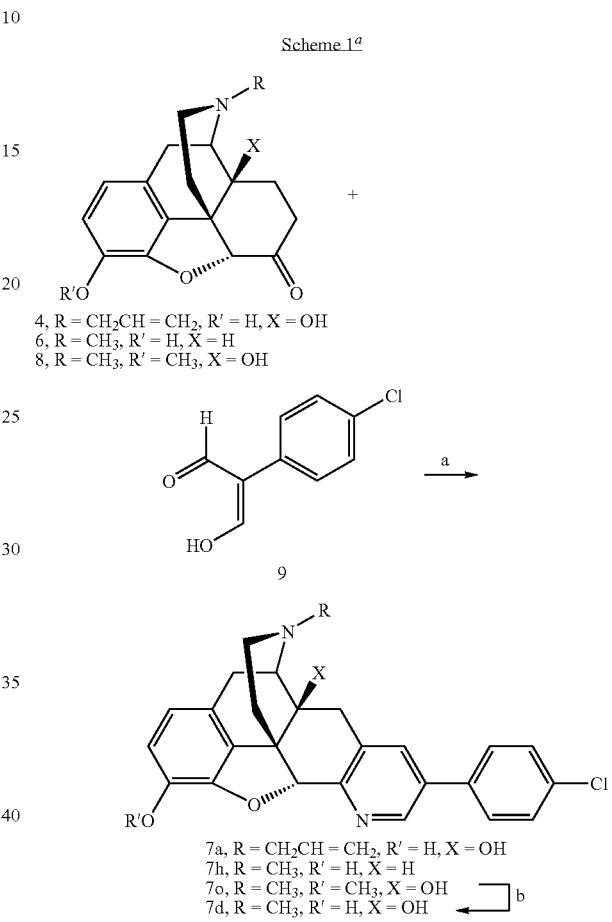

Scheme 1ᵃ

4, R = CH₂CH = CH₂, R' = H, X = OH
6, R = CH₃, R' = H, X = H
8, R = CH₃, R' = CH₃, X = OH

7a, R = CH₂CH = CH₂, R' = H, X = OH
7h, R = CH₃, R' = H, X = H
7o, R = CH₃, R' = CH₃, X = OH
7d, R = CH₃, R' = H, X = OH

ᵃReagents and reaction conditions: (a) AcONH₄, AcOH, reflux, 18 h; (b) BBr₃, CH₂Cl₂, -20° C., 4 h.

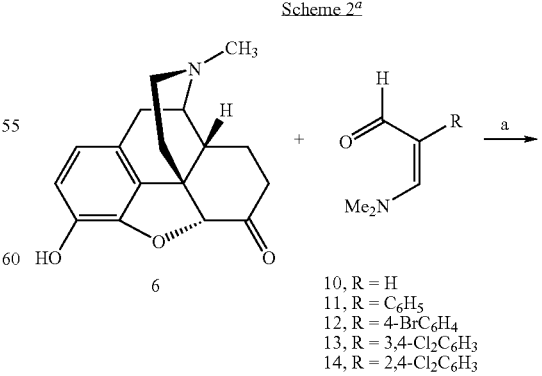

Scheme 2ᵃ

10, R = H
11, R = C₆H₅
12, R = 4-BrC₆H₄
13, R = 3,4-Cl₂C₆H₃
14, R = 2,4-Cl₂C₆H₃

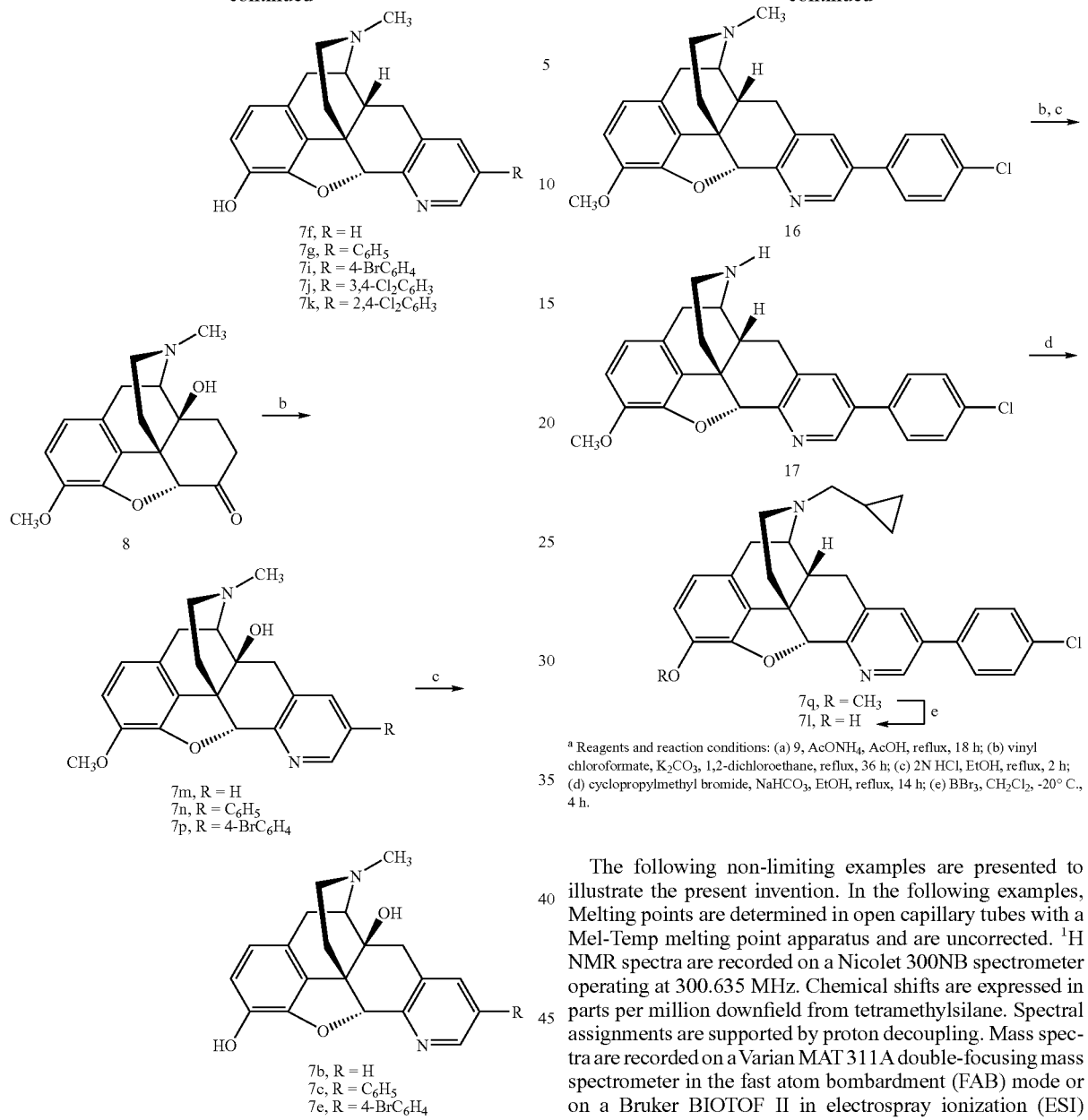

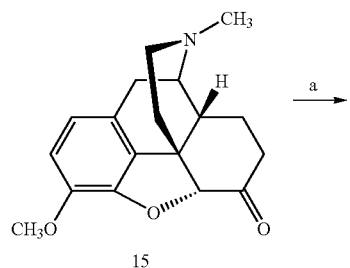

The following non-limiting examples are presented to illustrate the present invention. In the following examples, Melting points are determined in open capillary tubes with a Mel-Temp melting point apparatus and are uncorrected. $^1$H NMR spectra are recorded on a Nicolet 300NB spectrometer operating at 300.635 MHz. Chemical shifts are expressed in parts per million downfield from tetramethylsilane. Spectral assignments are supported by proton decoupling. Mass spectra are recorded on a Varian MAT 311A double-focusing mass spectrometer in the fast atom bombardment (FAB) mode or on a Bruker BIOTOF II in electrospray ionization (ESI) mode. Analytical results indicated by elemental symbols are within ±0.4% of the theoretical values. Thin layer chromatography (TLC) is performed on Analtech silica gel GF 0.25 mm plates. Flash column chromatography is performed with E. Merck silica gel 60 (230-400 mesh). Yields are of purified compounds and are not optimized.

EXAMPLE 1

17-(Allyl)-6,7-didehydro-3,14-dihydroxy-4,5α-epoxy-5'-(4-chlorophenyl)pyrido[2',3':6,7]morphinan (7a). A solution of naloxone hydrochloride (1.0 g, 2.74 mmol), 2-(4-chlorophenyl)malondialdehdye (0.552 g, 3.02 mmol) and ammonium acetate (0.421 g, 5.48 mmol) in AcOH (20 mL) is heated to reflux in an oil bath at 130-135° C. under an argon atmosphere for 18 h. The reaction mixture is cooled to room temperature and the solvent is removed under reduced pressure. The residue is treated with water and the pH of the mixture is adjusted to 8 with saturated aqueous NaHCO$_3$ solution. The solid that separated is collected by filtration, dissolved in CH$_2$Cl$_2$ and washed with brine. The organic layer is dried (Na$_2$SO$_4$), filtered, and the solvent is removed under reduced pressure. The crude product is chromatographed over a column of silica, using CHCl$_3$-MeOH—NH$_4$OH (98.5:0.1:0.5) as the eluent to obtain (0.385 g, 30%) of the desired product 7a: mp 168-172° C.; TLC, R$_f$ 0.2 (CH$_2$Cl$_2$-MeOH—NH$_4$OH, 97:2.5:0.5); $^1$H NMR (CDCl$_3$) δ 1.82-1.85 (m, 1H, C-16 H), 2.31-2.43 (m, 2H, C-15 H, C-16 H), 2.62 (m, 4H, C-8 H$_2$, C-10 H, C-15 H), 3.11-3.25 (m, 4H, C-9 H, C-10 H, CH$_2$ CH=CH$_2$), 4.80-5.50 (broad hump, 2H, C-3 OH, C-14, OH), 5.18-5.28 (m, 2H, CH=CH$_2$), 5.59 (s, 1H, C-5 H), 5.78-5.91 (m, 1H, CH=CH$_2$), 6.59 (d, 1H, J=8.1 Hz, C-1 H), 6.68 (d, 1H, J=8.1 Hz, C-2 H), 7.37-7.45 (m, 4H, C-2" H, C-3" H, C-5" H, C-6" H), 7.47 (d, 1H, J=2.1 Hz, C-4' H), 8.69 (d, 1H, J=1.8 Hz, C-6' H); MS m/z 473 (MH)$^+$. Anal. (C$_{28}$H$_{25}$ClN$_2$O$_3$.0.1H$_2$O) C, H, N.

EXAMPLE 2

6,7-Didehydro-3,14-dihydroxy-4,5α-epoxy-17-methylpyrido[2',3':6,7]morphinan (7b). Oxycodone hydrochloride (2.0 g, 5.69 mmol), 3-(dimethylamino)acrolein (0.845 g, 8.52 mmol) and ammonium acetate (1.31 g, 17.04 mmol) and AcOH (30 mL) is refluxed in an oil bath at 130-135° C. under an atmosphere of argon for 18 h. Work up of the reaction mixture and purification of the crude product as described above for the preparation of 7a gives 6,7-Didehydro-4,5α-epoxy-14-hydroxy-3-methoxy-17-methylpyrido[2',3':6,7]morphinan (7m) (0.792 g, 40%): mp 210-212° C.; TLC, R$_f$ 0.4 (CH$_2$Cl$_2$-MeOH—NH$_4$OH, 94.5:5:0.5); $^1$H NMR (CDCl$_3$) δ 1.80-1.83 (m, 1H, C-15 H), 2.35-2.40 (m, 2H, C-15 H, C-16 H), 2.43 (s, 3H, NCH$_3$), 2.50-2.78 (m, 4H, C-8 H$_2$, C-10 H, C-16 H), 2.95 (d, 1H, J=6.5 Hz, C-9 H), 3.26 (d, 1H, J=18.7 Hz, C-10 H), 3.79 (s, 3H, OCH$_3$), 4.5-5.8 (broad hump, 1H, C-14 OH), 5.53 (s, 1H, C-5 H), 6.61 (d, 1H, J=8.1 Hz, C-2 H), 6.66 (d, 1H, J=8.1 Hz, C-1 H), 7.10 (dd, 1H, J=7.7 and 4.6 Hz, C-5' H), 7.34 (d, 1H, J=7.7 Hz, C-4' H), 8.56-8.58 (m, 1H, C-6' H); ESI MS m/z 351 (MH)$^+$. Anal. (C$_{21}$H$_{22}$N$_2$O$_3$.0.2H$_2$O) C, H, N.

A solution of 7m (0.67 g, 1.91 mmol) in dichloromethane (25 ml) is cooled to −78° C. and treated dropwise with BBr$_3$ (19.0 mL of 1 M solution in CH$_2$Cl$_2$, 19.0 mmol). After 30 minutes the reaction is allowed to warm to −15 to −20° C. and is stirred for 4 h. The mixture is then treated with Et$_2$O (2 mL) and allowed to warm to room temperature. After stirring for an additional 30 min, the mixture is diluted with water and extracted twice with CH$_2$Cl$_2$ The organic layer is washed with brine and dried (N$_2$SO$_4$). The solvents are removed under reduced pressure and the crude product obtained is chromatographed over a column of silica, using CH$_2$Cl$_2$-MeOH—NH$_4$OH (97.5:2:0.5) as the eluent to obtain (0.179 g, 28%) of 7b: mp>230° C.; TLC, R$_f$ 0.3 (CH$_2$Cl$_2$-MeOH—NH$_4$OH, 94.5:5:0.5); $^1$H NMR(Me$_2$SO-d$_6$) δ 1.52-1.56 (m, 1H, C-15 H), 2.14-2.32 (m, 2H, C-15 H, C-16 H), 2.35 (s, 3H, NCH$_3$), 2.44-2.62 (m, 4H, C-8 H$_2$, C-10 H, C-16 H), 2.91 (d, 1H, J=6.1 Hz, C-9 H), 3.16 (d, 1H, J=18.6 Hz, C-10 H), 4.75 (s, 1H, C-14 OH), 5.28 (s, 1H, C-5 H), 6.49-6.54 (m, 2H, C-1 H, C-2 H), 7.23 (dd, 1H, J=7.7 and 4.7 Hz, C-5' H), 7.46 (dd, 1H, J=7.7 and 1.4 Hz, C-4' H), 8.48 (dd, 1H, J=4.7 and 1.5 Hz, C-6' H), 9.01 (s, 1H, C-3 OH); ESI MS m/z 337 (MH)$^+$. Anal. (C$_{20}$H$_{20}$N$_2$O$_3$.0.3H$_2$O) C, H, N.

EXAMPLE 3

6,7-Didehydro-3,14-dihydroxy-4,5α-epoxy-17-methyl-5'-phenylpyrido[2',3':6,7]morphinan (7c). Oxycodone hydrochloride (2.0 g, 5.68 mmol), is reacted with 3-(dimethylamino)-2-phenylacrolein (1.40 g, 8.52 mmol) (see Coppola et al. Synthesis and Reaction of 2-Aryl-3-(dimethylamino) acroleins. J. Heterocycl. Chem. 1974, 11, 51-56) and ammonium acetate (1.31 g, 17.04 mmol) in acetic acid (20 mL) by the same procedure as described for the preparation of 7a to obtain 6,7-didehydro-4,5α-epoxy-14-hydroxy-3-methoxy-17-methyl-5'-phenylpyrido[2',3':6,7]-morphinan (7n) (1.325 g, 55%): mp>250° C.; TLC, R$_f$ 0.5 (CH$_2$Cl$_2$-MeOH—NH$_4$OH, 96.5:3:0.5); $^1$H NMR (CDCl$_3$) δ 1.82-1.86 (m, 1H, C-15 H), 2.37-2.42 (m, 2H, C-15 H, C-16 H), 2.44 (s, 3H, NCH$_3$), 2.52-2.84 (m, 4H, C-8 H$_2$, C-10 H, C-16 H), 2.99 (d, 1H, J=6.4 Hz, C-9 H), 3.28 (d, 1H, J=18.7 Hz, C-10 H), 3.82 (s, 3H, OCH$_3$), 5.58 (s, 1H, C-5 H), 6.63 (d, 1H, J=8.1 Hz, C-2 H), 6.68 (d, 1H, J=8.1 Hz, C-1 H), 7.37-7.53 (m, 6H, C-4' H, C-5' phenyl-H), 8.79-8.78 (m, 1H, C-6' H); ESI MS m/z 427 (MH)$^+$. Anal. (C$_{27}$H$_{26}$N$_2$O$_3$.0.2H$_2$O) C, H, N.

The methyl ether 7n (0.189 g, 0.44 mmol) in CH$_2$Cl$_2$ (10 mL) is reacted with BBr$_3$ (4.4 mL of 1 M solution in CH$_2$Cl$_2$, 4.4 mmol) as described for the preparation of 7b from 7m to yield 0.112 g (61%) of 7c: mp 190-192° C.; TLC, R$_f$ 0.3 (CH$_2$Cl$_2$-MeOH—NH$_4$OH, 96.5:3:0.5); $^1$H NMR (CDCl$_3$) δ 1.82-1.85 (m, 1H, C-15 H), 2.38-2.42 (m, 2H, C-15 H, C-16 H), 2.44 (s, 3H, NCH$_3$), 2.53-2.82 (m, 4H, C-8 H$_2$, C-10 H, C-16 H), 2.98 (d, 1H, J=6.4 Hz, C-9 H), 3.27 (d, 1H, J=18.7 Hz, C-10 H), 4.2-5.68 (broad hump, 2H, C-3 OH, C-14 OH), 5.59 (s, 1H, C-5 H), 6.60 (d, 1H, J=8.1 Hz, C-2 H), 6.69 (d, 1H, J=8.1 Hz, C-1 H), 7.37-7.51 (m, 6H, C-4' H, C-5' phenyl-H), 8.72-8.73 (m, 1H, C-6' H); ESI MS m/z 413 (MH)$^+$. Anal. (C$_{26}$H$_{24}$N$_2$O$_3$.0.3H$_2$O) C, H, N.

EXAMPLE 4

5'-(4-Chlorophenyl)-6,7-didehydro-3,14-dihydroxy-4,5α-epoxy-17-methylpyrido[2',3':6,7]morphinan (7d). Oxycodone hydrochloride (1.0 g, 2.84 mmol), is reacted with 2-(4-chlorophenyl)malondialdehdye (0.584 g, 3.13 mmol) and ammonium acetate (0.438 g, 5.68 mmol) in acetic acid (20 mL) by the same procedure as described for the preparation of 7a to obtain 5'-(4-chlorophenyl)-6,7-didehydro-4,5α-epoxy-14-hydroxy-3-methoxy-17-methyl-pyrido[2',3':6,7]morphinan (7o) (0.527 g, 40%): mp 112-114° C.; TLC, R$_f$ 0.3 (CH$_2$Cl$_2$-MeOH—NH$_4$OH, 96.5:3:0.5); $^1$H NMR (CDCl$_3$) δ 1.82-1.86 (m, 1H, C-15 H), 2.37-2.41 (m, 2H, C-15 H, C-16 H), 2.44 (s, 3H, NCH$_3$), 2.52-2.83 (m, 4H, C-8 H$_2$, C-10 H, C-16 H), 2.98 (d, 1H, J=6.4 Hz, C-9 H), 3.29 (d, 1H, J=18.7 Hz, C-10 H), 3.81 (s, 3H, OCH$_3$), 4.7-4.8 (broad s, 1H, C-14 OH), 5.57 (s, 1H, C-5 H), 6.63 (d, 1H, J=8.1 Hz, C-2 H), 6.68 (d, 1H, J=8.1 Hz, C-1 H), 7.34-7.47 (m, 5H, C-4' H, C-2" H, C-3" H, C-5" H, C-6" H), 8.74 (d, 1H, J=2.1 Hz, C-6' H); ESI MS m/z 461 (MH)$^+$. Anal. (C$_{27}$H$_{25}$ClN$_2$O$_3$.0.1H$_2$O) C, H, N.

The methyl ether 7o (0.352 g, 0.76 mmol) in CH$_2$Cl$_2$ (15 mL) is reacted with BBr$_3$ (7.6 mL of 1 M solution in CH$_2$Cl$_2$, 7.6 mmol) as described for the preparation of 7b from 7m to yield 0.132 g (39%) of 7d: mp 196-198° C.; TLC, R$_f$ 0.3 (CH$_2$Cl$_2$-MeOH—NH$_4$OH, 94.5:5:0.5) $^1$H NMR (CDCl$_3$) δ 1.80-1.88 (m, 1H, C-15 H), 2.34-2.40 (m, 2H, C-15 H, C-16 H), 2.44 (s, 3H, NCH$_3$), 2.49-2.81 (m, 4H, C-8 H$_2$, C-10 H, C-16 H), 2.98 (d, 1H, J=6.4 Hz, C-9 H), 3.27 (d, 1H, J=18.7 Hz, C-10 H), 4.8-5.7 (broad hump, 2H, C-3 OH, C-14 OH), 5.58 (s, 1H, C-5 H), 6.61 (d, 1H, J=8.1 Hz, C-2 H), 6.69 (d, 1H, J=8.1 Hz, C-1 H), 7.34-7.44 (m, 4H, C-2" H, C-3" H, C-5" H, C-6" H), 7.47 (d, 1H, J=2.0 Hz, C-4' H), 8.69 (d, 1H, J=2.0 Hz, C-6' H); ESI MS m/z 447 (MH)$^+$. Anal. (C$_{26}$H$_{23}$ClN$_2$O$_3$.0.5H$_2$O) C, H, N.

EXAMPLE 5

5'-(4-Bromophenyl)-6,7-didehydro-3,14-dihydroxy-4,5α-epoxy-17-methylpyrido[2',3':6,7]morphinan (7e). Oxycodone hydrochloride (2.0 g, 5.68 mmol), is reacted with 2-(4-bromophenyl)-3-(dimethylamino)acrolein (2.16 g, 8.52 mmol) see Stacey et al. Pyridine Derivatives Inducing Tillering and Agricultural Compositions Containing Them. Eur. Pat. Appl. 67511, 1982; *Chem. Abstr.* 1983, 98, 198028) and ammonium acetate (1.31 g, 17.04 mmol) in acetic acid (30 mL) by the same procedure as described for the preparation of 7a to obtain 5'-(4-bromophenyl)-6,7-didehydro-4,5α-epoxy-14-hydroxy-3-methoxy-17-methyl-pyrido[2',3':6,7]morphinan (7p) (0.79 g, 28%): mp>230° C.; TLC, R$_f$ 0.4 (CH$_2$Cl$_2$-MeOH—NH$_4$OH, 94.5:5:0.5); $^1$H NMR (CDCl$_3$) δ 1.82-1.85 (m, 1H, C-15 H), 2.37-2.41 (m, 2H, C-15 H, C-16 H), 2.44 (s, 3H, NCH$_3$), 2.51-2.83 (m, 4H, C-8 H$_2$, C-10 H, C-16 H), 2.98 (d, 1H, J=6.4 Hz, C-9 H), 3.28 (d, 1H, J=18.7 Hz, C-10 H), 3.81 (s, 3H, OCH$_3$), 4.5-5.2 (broad hump, 1H, C-14 OH), 5.56 (s, 1H, C-5 H), 6.63 (d, 1H, J=8.1 Hz, C-2 H), 6.68 (d, 1H, J=8.1 Hz, C-1 H), 7.36-7.40 (m, 2H, C-2" H, C-6" H), 7.46 (d, 1H, J=2.1 Hz, C-4' H), 7.54-7.59 (m, 2H, C-3" H, C-5" H), 8.74 (d, 1H, J=2.1 Hz, C-6' H); ESI MS m/z 505 (MH)$^+$. Anal. (C$_{27}$H$_{25}$BrN$_2$O$_3$) C, H, N.

The methyl ether 7p (0.508 g, 1.0 mmol) in CH$_2$Cl$_2$ (20 mL) is reacted with BBr$_3$ (10.0 mL of 1 M solution in CH$_2$Cl$_2$, 10.0 mmol) as described for the preparation of 7b from 7m to yield 0.198 g (40%) of 7e: mp 196-198° C.; TLC, R$_f$ 0.3 (CH$_2$Cl$_2$-MeOH—NH$_4$OH, 94.5:5:0.5); $^1$H NMR (CDCl$_3$) δ 1.82-1.85 (m, 1H, C-15 H), 2.38-2.41 (m, 2H, C-15 H, C-16 H), 2.44 (s, 3H, NCH$_3$), 2.53-2.81 (m, 4H, C-8 H$_2$, C-10 H, C-16 H), 2.97 (d, 1H, J=6.4 Hz, C-9 H), 3.27 (d, 1H, J=18.7 Hz, C-10 H), 4.4-5.8 (broad hump, 2H, C-3 OH, C-14 OH), 5.57 (s, 1H, C-5 H), 6.61 (d, 1H, J=8.1 Hz, C-2 H), 6.69 (d, 1H, J=8.1 Hz, C-1 H), 7.34-7.38 (m, 2H, C-2" H, C-6" H), 7.48 (d, 1H, J=2.0 Hz, C-4' H), 7.54-7.58 (m, 2H, C-3" H, C-5" H), 8.68 (d, 1H, J=2.0 Hz, C-6' H); ESI MS m/z 491 (MH)$^+$. Anal. (C$_{26}$H$_{23}$BrN$_2$O$_3$.0.25H$_2$O) C, H, N.

EXAMPLE 6

6,7-Didehydro-4,5α-epoxy-3-hydroxy-17-methylpyrido[2',3':6,7]morphinan (7f). Hydromorphone hydrochloride (1.0 g, 3.10 mmol), 3-(dimethylamino)acrolein (0.369 g, 3.72 mmol) and ammonium acetate (0.477 g, 6.20 mmol) and AcOH (20 mL) is refluxed in an oil bath at 130-135° C. for 18 h. Work up of the reaction mixture and purification of the crude product as described for the preparation of 7a gives the desired product 7f (0.215 g, 22%): mp 164-166° C.; TLC, R$_f$ 0.3 (CH$_2$Cl$_2$-MeOH—NH$_4$OH, 95:4.5:0.5); $^1$H NMR (CDCl$_3$) δ 2.01-2.34 (m, 2H, C-15 H$_2$), 2.54-2.77 (m, 6H, C-8 H$_2$, C-10 H, C-14 H, C-16 H$_2$), 2.69 (s, 3H, NCH$_3$), 3.16 (d, 1H, J=18.7 Hz, C-10 H), 3.39-3.41 (m, 1H, C-9 H), 5.51 (s, 1H, C-5 H), 6.58 (d, 1H, J=8.1 Hz, C-2 H), 6.66 (d, 1H, J=8.1 Hz, C-1 H), 7.15 (dd, 1H, J=7.8 and 4.7 Hz, C-5' H), 7.34 (m, 1H, C-4' H), 8.52 (dd, 1H, J=4.7 and 1.1 Hz, C-6' H), 8.52-8.58 (br s, 1H, C-3 OH); ESI MS m/z 321 (MH)$^+$ Anal. (C$_{20}$H$_{20}$N$_2$O$_2$.0.6H$_2$O) C, H, N.

EXAMPLE 7

6,7-Didehydro-4,5α-epoxy-3-hydroxy-17-methyl-5'-phenylpyrido[2',3':6,7]morphinan (7g). Hydromorphone hydrochloride (1.0 g, 3.10 mmol) is reacted with 3-(dimethylamino)-2-phenylacrolein (0.651 g, 3.72 mmol)(see Coppola et al. supra) and ammonium acetate (0.477 g, 6.20 mmol) in acetic acid (20 mL) by the same procedure as described for the preparation of 7a to obtain 7g (0.54 g, 44%): mp 182-184° C.; TLC, R$_f$ 0.3 (CH$_2$Cl$_2$-MeOH—NH$_4$OH, 95:4.5:0.5); $^1$H NMR (CDCl$_3$) δ 1.95-2.14 (m, 2H, C-15 H$_2$), 2.31-2.67 (m, 6H, C-8 H$_2$, C-10 H, C-14 H, C-16 H$_2$), 2.46 (s, 3H, NCH$_3$), 3.11 (d, 1H, J=18.7 Hz, C-10 H), 3.29-3.31 (m, 1H, C-9 H), 4.8-5.6 (broad hump, 1H, C-3 OH), 5.58 (s, 1H, C-5 H), 6.61 (d, 1H, J=8.1 Hz, C-2 H), 6.68 (d, 1H, J=8.1 Hz, C-1 H), 7.35-7.52 (m, 6H, C-4' H, C-5'-phenyl-H), 8.74 (d, 1H, J=1.6 Hz, C-6' H); ESI MS m/z 397 (MH)$^+$. Anal. (C$_{26}$H$_{24}$N$_2$O$_2$.0.6H$_2$O) C, H, N.

EXAMPLE 8

5'-(4-Chlorophenyl)-6,7-didehydro-4,5α-epoxy-3-hydroxy-17-methylpyrido[2',3':6,7]morphinan (7h). Hydromorphone hydrochloride (10.0 g, 31.1 mmol), is reacted with 2-(4-chlorophenyl)malondialdehdye (6.81 g, 37.3 mmol) and ammonium acetate (4.79 g, 62.2 mmol) in acetic acid (140 mL) by the same procedure as described for the preparation of 7a to obtain (7h) (3.033 g, 23%): mp 188-190° C.; TLC, R$_f$ 0.35 (CH$_2$Cl$_2$-MeOH—NH$_4$OH, 96.5:3:0.5); $^1$H NMR (CDCl$_3$) δ 1.97-2.14 (m, 2H, C-15 H$_2$), 2.30-2.48 (m, 3H, C-8 H, C-10 H, C-16 H), 2.46 (s, 3H, NCH$_3$), 2.55-2.64 (m, 3H, C-8 H, C-14 H, C-16 H), 3.11 (d, 1H, J=18.6 Hz, C-10 H), 3.28-3.30 (m, 1H, C-9 H), 5.57 (s, 1H, C-5 H), 6.60 (d, 1H, J=8.1 Hz, C-2 H), 6.68 (d, 1H, J=8.1 Hz, C-1 H), 7.40-7.46 (m, 5H, C-4' H, C-2" H, C-3" H, C-5" H, C-6" H), 8.72 (d, 1H, J=2.1 Hz, C-6' H); ESI MS m/z 431 (MH)$^+$. Anal. (C$_{26}$H$_{23}$ClN$_2$O$_2$) C, H, N.

A solution of the compound in EtOH is treated with a 2M solution of hydrogen chloride in Et$_2$O. Removal of the solvent under reduced pressure and trituration with Et$_2$O gives the 7h.2HCl salt: mp 276-278° C. dec; ESI MS m/z 431 (MH)$^+$. Anal. (C$_{26}$H$_{23}$ClN$_2$O$_2$.2HCl.2H$_2$O) C, H, N.

EXAMPLE 9

5'-(4-Bromophenyl)-6,7-didehydro-4,5α-epoxy-3-hydroxy-17-methylpyrido[2',3':6,7]morphinan (7i). Hydromorphone hydrochloride (3.0 g, 9.32 mmol), is reacted with 2-(4-bromophenyl)-3-(dimethylamino)acrolein (2.60 g, 10.25 mmol) (see Stacey et al.,supra) and ammonium acetate (1.45 g, 18.64 mmol) in acetic acid (60 mL) by the same procedure as described for the preparation of 7a to obtain 7i (0.93 g, 21%): mp 186-188° C.; TLC, R$_f$0.3 (CH$_2$Cl$_2$-MeOH—NH$_4$OH, 94.5:5:0.5); $^1$H NMR (CDCl$_3$) δ 1.99-2.13 (m, 2H, C-15 H$_2$), 2.27-2.44 (m, 1H, C-16H), 2.46 (s, 3H, NCH$_3$), 2.33-3.08 (broad hump, 2H, C-3 OH, C-14 H), 2.49-2.65 (m, 4H, C-8 H$_2$, C-10 H, C-16 H), 3.11 (d, 1H, J=18.7 Hz, C-10 H), 3.31 (dd, 1H, J=5.8 and 2.4 Hz, C-9 H), 5.55 (s, 1H, C-5 H), 6.61 (d, 1H, J=8.1 Hz, C-2 H), 6.68 (d, 1H, J=8.1 Hz, C-1 H), 7.31-7.35 (m, 2H, C-3" H, C-5" H), 7.41 (d, 1H, J=2.0 Hz, C-4' H), 7.53-7.57 (m, 2H, C-2 H", C-6 H"), 8.65 (d, 1H, J=2.0 Hz, C-6 H'); ESI MS m/z 475 (MH)$^+$. Anal. (C$_{26}$H$_{23}$BrN$_2$O$_2$.0.5H$_2$O) C, H, N.

EXAMPLE 10

5'-(3,4-Dichlorophenyl)-6,7-didehydro-4,5α-epoxy-3-hydroxy-17-methylpyrido[2',3':6,7]morphinan (7j). Hydromorphone hydrochloride (1.00 g, 3.1 mmol), is reacted with 2-(3,4-dichlorophenyl)-3-(dimethylamino)acrolein (see Coppola et al., supra) (1.135 g, 4.65 mmol) and ammonium acetate (0.478 g, 6.2 mmol) in acetic acid (20 mL) by the same procedure as described for the preparation of 7a to obtain 7j (0.25 g, 17%): mp 184-186° C.; TLC, $R_f$ 0.3 ($CH_2Cl_2$-MeOH—$NH_4OH$, 94.5:5:0.5); $^1H$ NMR ($CDCl_3$) δ 1.97-2.14 (m, 2H, C-15 $H_2$), 2.30-2.48 (m, 3H, C-8 H, C-10 H, C-16 H), 2.46 (s, 3H, $NCH_3$), 2.55-2.64 (m, 3H, C-8 H, C-14 H, C-16 H), 3.12 (d, 1H, J=18.7 Hz, C-10 H), 3.27-3.30 (m, 1H, C-9 H), 4.8-5.6 (broad hump, 1H, C-3 OH), 5.57 (s, 1H, C-5 H), 6.61 (d, 1H, J=8.1 Hz, C-2 H), 6.68 (d, 1H, J=8.1 Hz, C-1 H), 7.34 (dd, 1H, J=8.3 and 2.1 Hz, C-5 H), 7.44 (d, 1H, J=1.9 Hz, C-4 H'), 7.52 (d, 1H, J=8.3 Hz, C-6" H), 7.59 (d, 1H, J=2.2, C-2" H), 8.70 (d, 1H, J=1.8 Hz, C-6' H); ESI MS m/z 465 (MH)$^+$. Anal. ($C_{26}H_{22}Cl_2N_2O_2 \cdot 0.5H_2O$) C, H, N.

EXAMPLE 11

5'-(2,4-Dichlorophenyl)-6,7-didehydro-4,5α-epoxy-3-hydroxy-17-methylpyrido[2',3':6,7]morphinan (7k). Hydromorphone hydrochloride (1.00 g, 3.1 mmol), is reacted with 2-(2,4-dichlorophenyl)-3-(dimethylamino)acrolein (1.135 g, 4.65 mmol) (see Biziere et al. Heterocyclic Nitrogen Compounds. Eur. Pat. Appl. 169139, 1986; *Chem. Abstr.* 1986, 105, 97319) and ammonium acetate (0.716 g, 9.3 mmol) in acetic acid (20 mL) by the same procedure as described for the preparation of 7a to obtain 7k (0.464 g, 32%): mp 198-200° C.; TLC, $R_f$ 0.3 ($CH_2Cl_2$-MeOH—$NH_4OH$, 94.5:5:0.5); $^1H$ NMR ($CDCl_3$) δ 1.96-2.15 (m, 2H, C-15 $H_2$), 2.30-2.71 (m, 6H, C-8 $H_2$, C-10 H, C-14 H, C-16 $H_2$), 2.46 (s, 3H, $NCH_3$), 3.11 (d, 1H, J=18.7 Hz, C-10 H), 3.33-3.30 (m, 1H, C-9 H), 5.56 (s, 1H, C-5 H), 6.61 (d, 1H, J=8.1 Hz, C-2 H), 6.69 (d, 1H, J=8.1 Hz, C-1 H), 7.20 (d, 1H, J=8.4 Hz, C-6" H), 7.31 (dd, 1H, J=8.2 and 2.1 Hz, C-5" H), 7.38 (d, 1H, J=2.0 Hz, C-4' H), 7.49 (d, 1H, J=2.1 Hz, C-3" H), 8.58 (d, 1H, J=1.8 Hz, C-6' H); ESI MS m/z 465 (MH)$^+$. Anal. ($C_{26}H_{22}Cl_2N_2O_2 \cdot 0.5H_2O$) C, H, N.

EXAMPLE 12

5'-(4-Chlorophenyl)-17-(cyclopropylmethyl)-6,7-didehydro-4,5α-epoxy-3-hydroxypyrido[2',3':6,7]morphinan (7l). Hydrocodone (5.838 g, 19.52 mmol), obtained from the bitartrate salt by conventional methods, is reacted with 2-(4-chlorophenyl)malondialdehdye (5.46 g, 29.28 mmol) and ammonium acetate (4.51 g, 58.56 mmol) in acetic acid (100 mL) by the same procedure as described for the preparation of 7a to obtain 5'-(4-chlorophenyl)-6,7-didehydro-4,5α-epoxy-3-methoxy-17-methylpyrido[2',3':6,7]morphinan (16) (4.70 g, 55%): mp 234-237° C.; TLC, $R_f$ 0.57 ($CHCl_3$-MeOH, 9:1); $^1H$ NMR ($CDCl_3$) 1.99-2.13(m, 2H, C-15 H, C-16 H), 2.32-2.54 (m 3H, C-8 H, C-10 H, C-16 H), 2.46 (s, 3H, $NCH_3$), 2.55-2.64 (m, 3H, C-8H, C-10 H, C-16 H), 3.18 (d, 1H, J=18.5 Hz, C-10 H), 3.25-3.28 (m, 1H, C-9 H), 3.8 (s, 3H, $OCH_3$), 5.5 (s, 1H, C-5 H), 6.64 (d, 1H, J=8.2 Hz, C-1 H), 6.69 (d, 1H, J=8.20 Hz, C-2 H), 7.5-7.6 (m, 2H, C-3" H, C-5" H), 7.70-7.73 (m, 3H, C-3' H, C-2" H, C-6" H), 8.74 (d, 1H, J=2.3 Hz, C-6' H); ESI MS m/z 445 (MH)$^+$. Anal. ($C_{27}H_{25}ClN_2O_2 \cdot 0.2H_2O$) C, H, N.

To a solution of compound 16 (2.85 g, 6.61 mmol) in 1,2-dichloroethane (50 ml) potassium carbonate (3.11 g, 22.5 mmol) is added. The mixture is stirred in an inert atmosphere and vinyl chloroformate (4.1 g, 38.52 mmol) is added dropwise. The reaction mixture is refluxed for 36 h and filtered. The filtrate is evaporated to dryness and the residue is dissolved in ethanol (15 ml). To this solution is added 2N HCl (5.0 mL) and the mixture is refluxed for 2 h. The solvent is removed under reduced pressure. The residue is treated with water and the pH of the mixture is adjusted to 7-8 by addition of saturated aqueous $NaHCO_3$ solution. The mixture is then extracted with $CHCl_3$ (4×100 mL). The extracts are combined, washed with brine and dried over anhydrous sodium sulfate. Filtration and removal of the solvent yield the crude product which is purified by chromatography over a column of silica using $CH_2Cl_2$-MeOH—$NH_4OH$ 98.5:1:0.5 as the eluent to obtain 5'-(4-chlorophenyl)-6,7-didehydro-4,5α-epoxy-3-methoxypyrido[2',3':6,7]-morphinan (17) (1.47 g, 53%): mp 246-248° C.; TLC, $R_f$ 0.44 ($CHCl_3$-MeOH, 9:1); $^1H$ NMR (DMSO-$d_6$) δ 1.69-1.73 (m, 1H, C-15 H), 1.82-1.92 (m,1H, C-15 H), 1.99-2.08 (m, 1H, C-16 H), 2.36-2.44 (m, 1H, C-14 H), 2.59-2.78 (m, 4H, C-8 $H_2$, C-10 H, C-16 H), 2.87-2.96 (m, 1H, C-10 H), 3.37-3.39 (m, 1H, C-9 H), 3.67 (s, 3H, $OCH_3$), 5.4 (s, 1H, C-5 H), 6.64 (d, 1H, J=8.2 Hz, C-1 H), 6.62 (d, 1H, J=8.13 Hz, C-2 H), 7.5-7.6 (m, 2H, C-3" H, C-5" H), 7.70-7.73 (m, 3H, C-3' H, C-2" H, C-6" H), 8.8 (d, 1H, J=2.09 Hz, C-6' H); ESI MS m/z 431 (MH)$^+$. Anal. ($C_{26}H_{23}ClN_2O_2 \cdot 0.4H_2O$) C, H, N.

Compound 17 (1.37 g, 3.19 mmol) is dissolved in ethanol (70 mL) and $NaHCO_3$ (5.33 g, 6.37 mmol) is added. To this mixture is added cyclopropylmethyl bromide (2.16 g, 16.0 mmol), and the reaction mixture is refluxed under nitrogen for 16 h. The mixture was then concentrated, and water (180 mL) is added to the residue. The mixture is extracted with $CHCl_3$ (4×100 mL) and dried over $Na_2CO_3$. Removal of the solvent under reduced pressure gives the crude product, which is purified by chromatography over a column of silica using $CH_2Cl_2$-MeOH—$NH_4OH$ (98.5:1:0.5) as the eluent to give 5'-(4-chlorophenyl)-17-(cyclopropylmethyl)-6,7-didehydro-4,5α-epoxy-3-methoxypyrido[2',3':6,7]morphinan (7q) (0.93 g, 76%): mp; 196-198° C.; TLC, $R_f$ 0.5 ($CH_2Cl_2$-MeOH—$NH_4OH$, 96.5:3:0.5); $^1H$ NMR ($CDCl_3$) δ 0.14-0.19 and 0.53-0.59 (2m, 4H, cyclopropyl $CH_2CH_2$), 0.85-0.89 (m, 1H, cyclopropyl CH), 1.97-2.15 (m, 2H, C-15 $H_2$), 2.28-2.66 (m, 7H, C-8 $H_2$, C-10 H, C-14 H, C-16 H, and $NCH_2$-cyclopropyl), 2.81-2.86 (m, 1H, C-16 H), 3.02 (d, 1H, J=18.7 Hz, C-10 H), 3.57-3.60 (m, 1H, C-9 H), 3.81 (s, 3H, $OCH_3$), 5.56 (s, 1H, C-5 H), 6.61 (d, 1H, J=8.1 Hz, C-2 H), 6.67 (d, 1H, J=8.1 Hz, C-1 H), 7.39-7.46 (m, 5H, C-4' H, C-2" H, C-3" H, C-5" H, C-6" H), 8.75 (d, 1H, J=1.6 Hz, C-6' H); ESI MS m/z 485 (MH)$^+$. Anal. ($C_{30}H_{29}ClN_2O_2$) C, H, N.

A solution of the methyl ether 7q (0.83 g, 1.71 mmol) in $CH_2Cl_2$ (20 mL) is reacted with $BBr_3$ (17.0 mL of 1 M solution in $CH_2Cl_2$, 17.0 mmol) as described for the preparation of 7b from 7m to yield 0.227 g (28%) of 7l: mp 178-180° C.; TLC, $R_f$ 0.3 ($CH_2Cl_2$-MeOH—$NH_4OH$, 96.5:3:0.5); $^1H$ NMR ($CDCl_3$) δ 0.13-0.19 and 0.51-0.57 (2m, 4H, cyclopropyl $CH_2CH_2$), 0.85-0.93 (m, 1H, cyclopropyl CH), 1.96-2.16 (m, 2H, C-15 $H_2$), 2.28-2.66 (m, 7H, C-8 $H_2$, C-10 H, C-14 H, C-16 H, and $NCH_2$-cyclopropyl), 2.82-2.87 (m, 1H, C-16 H), 3.00 (d, 1H, J=18.7 Hz, C-10 H), 3.60-3.62 (m, 1H, C-9 H), 5.2-5.8 (broad hump, 1H, C-3 OH), 5.57 (s, 1H, C-5 H), 6.58 (d, 1H, J=8.1 Hz, C-2 H), 6.67 (d, 1H, J=8.1 Hz, C-1 H), 7.39-7.45 (m, 5H, C-4' H, C-2" H, C-3" H, C-5" H, C-6" H), 8.70 (d, 1H, J=2.0 Hz, C-6' H); ESI MS m/z 471 (MH)$^+$. Anal. ($C_{29}H_{27}ClN_2O_2$) C, H, N.

EXAMPLE 13

17-(Cyclopropylmethyl)-6,7-didehydro-3,14-dihydroxy-4,5α-epoxy-6'-phenylpyridazino[3',4':6,7]morphinan (18). To a solution of naltrexone hydrochloride (0.378 g, 1.0 mmol) in methanol (14 mL) is added aqueous sodium hydroxide (1 N, 7.0 mL, 7.0 mmol) and phenylglyoxal (0.938 g, 7.0 mmol). The mixture is allowed to stand in the refrigerator for 16 h. The mixture is then neutralized with 1 N HCl and extracted with $CHCl_3$ (3×100 mL). The combined organic layers are ashed with brine and dried over anhydrous $Na_2SO_4$ and concentrated to afford a crude product. The crude product is taken in acetonitrile (5 mL) and hydrazine hydrate (0.119 g, 2.37 mmol) is added and the mixture is stirred at room temperature overnight. The solvent is removed under reduced pressure and the crude product is purified by chromatography over a column of silica using $CHCl_3$-MeOH, 98:2 as the eluent to obtain 18: Yield 0.08 g (18%), mp 162-164° C.; TLC, $R_f$ 0.74 ($CHCl_3$-MeOH, 9:1); $^1H$ NMR ($CDCl_3$) δ 0.14-0.21 and 0.54-0.63 (2m, 4H, cyclopropyl $CH_2CH_2$), 0.84-0.99 (m, 1H, cyclopropyl CH), 1.86-1.93 (m, 1H, C-15 H), 2.36-2.51 (m, 4H, C-15 H, C-16 H, and $NCH_2$-cyclopropyl), 2.63-2.81 (m, 4H, C-8 $H_2$, C-16 H, C-10H), 3.22 (d, 1H, J=18.7 Hz, C-10 H), 3.33 (d, 1H, J=6.48 Hz, C-9 H), 3.6-5.8 (broad hump, 2H, C-3 OH, C-14 OH), 5.85 (s, 1H, C-5 H), 6.61 (d, 1H, J=8.2 Hz, C-2 H), 6.71 (d, 1H, J=8.1 Hz, C-1 H), 7.52-7.46 (m, 4H, C-4' H, C-2' H, C-3' H, C-5'H), 7.97-8.02 (m, 2H, C-1' H, C-6' H); ESI MS m/z 454 (MH)$^+$. Anal. ($C_{28}H_{27}N_3O_3$.0.5$H_2O$) C, H, N.

EXAMPLE 14

17-(Cyclopropylmethyl)-6,7-didehydro-3,14-dihydroxy-4,5α-epoxy-6'-(4-chlorophenyl)pyridazino[3',4':6,7]morphinan (19). Naltrexone hydrochloride (0.378 g, 1.0 mmol) is reacted with 4-(chlorophenyl)glyoxal (0.746 g, 4 mmol) and then with hydrazine hydrate (0.124 g, 2.47 mmol) as described above for the preparation of 18 to obtain 19: Yield 0.07 g (14%), mp 172-174° C.; TLC, $R_f$ 0.47 ($CHCl_3$-MeOH, 95:5); $^1H$ NMR ($CDCl_3$) δ 0.13-0.22 and 0.55-0.63 (2m, 4H, cyclopropyl $CH_2CH_2$), 0.83-0.95 (m, 1H, cyclopropyl CH), 1.86-1.93 (m, 1H, C-15 H), 2.36-2.52 (m, 4H, C-15 H, C-16 H, and $NCH_2$-cyclopropyl), 2.64-2.81 (m, 4H, C-8 $H_2$, C-16 H, C-10H), 3.15 (d, 1H, J=18.6 Hz, C-10 H), 3.3 (d, 1H, J=6.6 Hz, C-9 H), 3.6-5.8 (broad hump, 2H, C-3 OH, C-14 OH), 5.84 (s, 1H, C-5 H), 6.59 (d, 1H, J=8.13 Hz, C-2 H), 6.68 (d, 1H, J=8.1 Hz, C-1 H), 7.44-7.47 (m, 3H, C-3" H, C-5" H, C-4' H), 7.93-7.96 (m, 2H, C-2" H, C-6" H); ESI MS m/z 488 (MH)$^+$. Anal. ($C_{28}H_{26}ClN_3O_3$.0.5 $CHCl_3$) C, H, N.

EXAMPLE 15

6,7-didehydro-4,5α-epoxy-3-hydroxy-17-methyl-6'-phenylpyridazino[3',4':6,7]morphinan (20). Hydromorphone hydrochloride (0.50 g, 1.56 mmol) is reacted with phenylglyoxal (0.988 g, 7.37 mmol) and then with hydrazine hydrate (0.195 g, 3.4 mmol) as described above for the preparation of 18 to obtain 20: Yield 0.16 g (26%), mp 204-206° C.; TLC, $R_f$ .0.47 ($CHCl_3$-MeOH 85:15); $^1H$ NMR (DMSO-$d_6$) δ1.72-1.79 (m, 1H, C-15 H), 2.00-2.52 (m, 6H, C-8 $H_2$, C-15 H, C-16 $H_2$, C-14 H), 2.33 (s, 3H, N—$CH_3$), 2.67 (dd, 1H, J=16.6 and 16.7 Hz, C-10 H), 2.96 (d, 1H, J=18.5 Hz, C-10H), 3.12-3.18 (m, 1H, C-9 H), 5.75 (s, 1H, C-5 H), 6.52-6.58 (m, 2H, C-1 H,C-2 H), 7.40-7.45 (m, 3H, C-3"H,C-5" H, C-4" H), 7.75 (s, 1H, C-4' H), 7.91-7.95 (m, 2H, C-2" H, C-6" H), 9.07 (s, 1H, C-3 OH); ESI MS m/z 398 (MH)$^+$. Anal. ($C_{25}H_{23}N_3O_2$.0.75 $H_2O$) C, H, N.

EXAMPLE 16

6,7-Didehydro-4,5α-epoxy-3-hydroxy-17-methyl-6'-(4-chlorophenyl)pyridazino[3',4':6,7]morphinan (21). Hydromorphone hydrochloride (1.0 g, 3.1 mmol) is reacted with (4-chlophenyl)glyoxal (2.32 g, 12.43 mmol) and then with hydrazine hydrate (0.232 g, 4.65 mmol) as described above for the preparation of 18 to obtain 30: Yield 0.195 g (15%), mp 178-180° C.; TLC, $R_f$ 0.39 ($CHCl_3$-MeOH 9:1); $^1H$ NMR ($CDCl_3$) δ 1.73-1.82 (m, 1H, C-15 H), 2.00-2.61 (m, 6H, C-8 $H_2$, C-14 H, C-15 H, C-16 $H_2$), 2.33 (s, 3H, N—$CH_3$), 2.61-2.76 (dd, 1H, J=15.8 and 16.7 Hz, C-10 H), 2.94-3.04 (d, 1H, J=18.7 Hz, C-10 H) 3.12-3.2 (m, 1H, C-9 H), 5.74 (s, 1H, C-5 H), 6.51-6.58 (m, 2H, C-1 H,C-2 H), 7.58-7.65 (m, 2H, C-3"H, C-5"H), 7.92 (s, 1H, C-4' H), 8.08-8.16 (m, 2H, C-2" H, C-6"H), 9.06 (s, 1H, C-3 OH); ESI MS m/z 432 (MH)$^+$. Anal. ($C_{25}H_{22}ClN_3O_2$.$H_2O$) C, H, N.

Biology

Opioid Receptor Binding. The binding affinities of the target compounds for the opiod δ and μ receptors are determined by inhibition of binding of [$^3H$]DADLE, (see Rothman et al., LY 164929: A Highly Selective Ligand for the Lower Afinity [$^3H$]D-Ala$^2$-D-Leu$^5$-Enkephalin Binding Sites. *Neuropeptides* 1988, 11, 13-16) and [$^3H$]DAMGO (see Rothman et al., RTI-4614-4: An Analog of (+)-cis-3-Methylfentanyl with a 27,000-fold Binding Selectivity for Mu Versus Delta Opioid Binding Sites. *Life Sci.* 1991, 48, PL111-PL116.) to rat brain membrances. [$^3H$]DADLE binding to μ receptors was blocked using 100 nM DAMGO. The affinities of the compounds for the κ receptors were determined by inhibition of binding [$^3H$]U69,593 (see Rothman et al., Interaction of Endogenous Opioid Peptides and Other Drugs with Four Kappa Opioid Binding Sites in Guinea Pig Brain. *Peptides* 1990, 1, 311-331.) to guinea pig brain membranes using previously reported procedures; (see Ananthan et al. (I); supra; Ananthan et al. (II); supra; Ananthan et al., Synthesis, Opioid Receptor Binding, and Bioassay of Naltrindole Analogues Substituted in the Indolic Benezene Moiety. *J. Med. Chem.* 1998, 41, 2872-2881.). The δ, μ and κ opioid receptor binding affinities along with binding selectivity ratios for the target compounds 7a-l are given in Table 1. The phenolic methyl ether compounds 7m-q are prepared as intermediates leading to the corresponding phenolic targets. These methyl ethers were also evaluated for their binding affinities. The affinity data for these ethers as well as the previously reported data for prior compounds 2a-c are also listed in Table 1.

Mu binding sites are labeled using [$^3H$]DAMGO (1-3 nM) and rat brain membranes as previously described (See Rothman et al. (II), supra) with several modifications. Rat membranes are prepared each day using a partially thawed frozen rat brain which was homogenized with a polytron in 10 mL/brain of ice-cold 10 mM Tris-HCl, pH 7.0. Membranes are then centrifuged twice at 30000 g for 10 min and resuspended with ice-cold buffer following each centrifugation. After the second centrifugation, the membranes are resuspended in 50 mM Tris-HCl, pH 7.4 (50 mL/brain), at 25° C. Incubations proceeded for 2 h at 25° C. in 50 mM Tris-HCl, pH 7.4, along with a protease inhibitor cocktail (PIC). The nonspecific binding was determined using 20 μM of levallorphan. Delta binding sites were labeled using [$^3H$]DADLE (2 nM) and rat brain membranes as previously described, (Rothman et al. III supra) with several modifications. Rat membranes are prepared each day using a partially thawed frozen rat brain which was homogenized with a polytron in 10 mL/brain of ice-cold 10 mM Tris-HCl, pH 7.0. Membranes were then centrifuged twice at 30000 g for 10 min and resuspended with ice-cold buffer following each centrifugation. After the second centrifugation, the membranes are resuspended in 50 mM Tris-HCl, pH 7.4 (50 mL/brain), at 25° C. Incubations proceeded for 2 h at 25° C. in 50 mM Tris-HCl, pH 7.4, containing 100 mM choline chloride, 3 mM $MnCl_2$, 100 nM DAMGO to block binding to μ sites, and PIC. Nonspecific binding is determined using 20 μM levallorphan. Kappa binding sites were labeled using [$^3H$]U69,593 (2 nM)

as previously described,[32] with several modifications. Guinea pig brain membranes were prepared each day using partially thawed guinea pig brain which was homogenized with a polytron in 10 mL/brain of ice-cold 10 mM Tris-HCl, pH 7.0. The membranes were then centrifuged twice at 30000 g for 10 min and resuspended with ice-cold buffer following each centrifugation. After the second centrifugation, the membranes are resuspended in 50 mM Tris-HCl, pH 7.4 (75 mL/brain), at 25° C. Incubations proceeded for 2 h at 25° C. in 50 mM Tris-HCl, pH 7.4, containing 1 μg/mL of captopril and PIC. Nonspecific binding is determined using 1 μM U69, 593. Each $^3$H ligand is displaced by 8-10 concentrations of test drug, two times. Compounds are prepared as 1 mM solution with 10 mM Tris buffer (pH 7.4) containing 10% DMSO before drug dilution. All drug dilutions are done in 10 mM Tris-HCl, pH 7.4, containing 1 mg/mL bovine serum albumin. All washes are done with ice-cold 10 mM Tris-HCl, pH 7.4.

[$^{35}$S]GTP-γ-S Binding Assays. All compounds are screened at a 10 μM concentration for agonist and antagonist activity at μ, δ and κ receptors in vitro using [$^{35}$S]GTP-γ-S binding assays in guinea pig caudate membranes as described previously. (See Thomas et al. (I), Optically Pure (−)-4-[(N-Allyl-3-methyl-4-piperidinyl)phenyl-amino]-N,N-diethyl-benzamide Displays Selective Binding and Full Agonist Activity for the Delta Opioid Receptor. *Bioorg. Med. Chem. Lett.* 1999, 9, 3347-3350; Thomas, et al. (II), Identification of an Opioid κ Receptor Subtype-Selective N-Substituent for (+)-(3R,4R)-Dimethyl-4-(3-hydroxyphenyl)piperidine. *J. Med. Chem.* 1998, 41, 5188-5197; and Partilla et al., Opioid Peptide Receptor Studies. 13. Characterization of Opioid Antagonists With the [$^{35}$S]GTP-γ-S Binding Assay. *Analgesia*, 1999, 4, 27-32.

Agonist activity is tested by measuring the stimulation of [$^{35}$S]GTP-γ-S binding by the compounds in the absence and presence of fixed concentrations of selective antagonists to block receptors other than the one being studied. The selective antagonist ligands used are: CTAP (2 nM) to block μ receptors, TIPP (1 μM) to block ι receptors, and nor-BNI (6 nM) to block κ receptors. (See Thomas et al. (I), supra). The antagonist properties of the compounds were determined by measuring the test compound's ability to inhibit stimulation of [$^{35}$S]GTP-γ-S binding produced by the selective agonists (10 μM): SNC-80 for δ receptor, DAMGO for μ receptor, and U69,593 for κ receptor. (See Thomas et al. II and Partilla et al., supra). Compounds are selected for more detailed study, using concentration-response curves, based on their binding $K_i$ values (Table 1) and their profile of agonist and antagonist activity in the initial [$^{35}$S]GTP-γ-S binding assay. The agonist efficacy of the compounds is expressed as a percent of stimulation compared to that produced by the standard agonist. The results are presented in Table 2.

The [$^{35}$S]-GTP-γ-S binding assay proceeded according to the methods described previously. (Thomas et al.(II)). Guinea pig caudate membranes (10 to 20 μg protein in 300 μL of 50 mM Tris-HCl, pH 7.4 with 1.67 mM DTT and 0.15% BSA) are added to polystyrene 96-well plates filled with 200 μL of a reaction buffer containing 50 mM Tris-HCl, pH 7.4, 100 mM NaCl, 10 mM MgCl$_2$, 1 mM EDTA, 100 μM GDP, 0.1% BSA, 0.05-0.01 nM [$^{35}$S]-GTP-γ-S and varying concentrations of drugs. The reaction mixture was incubated for 3 h at 22° C. (equilibrium). The reaction is terminated by the addition of 0.5 mL of ice-cold Tris-HCl, pH 7.4 (4° C.) followed by rapid vacuum filtration through Whatman GF/B filters previously soaked in ice-cold Tris-HCl, pH 7.4 (4° C.). The filters are washed twice with 0.5 mL of ice-cold H$_2$O (4° C.). Bound radioactivity was counted at an efficiency of 98% by liquid scintillation spectroscopy. Nonspecific binding is determined in the presence of 10 μM GTP-γ-S.

In initial screening experiments, each test agent is tested to determine agonist and antagonist activity using a 10 μM concentration in the absence and presence of selective antagonists (6000 nM CTAP, 6 nM nor-BNI or 20 nM NTI or 500 nM TIPP) and selective agonists (10 μM SNC80, 10 μM DAMGO or 10 μM U69,593). Compounds showing significant agonist activity are further characterized. In this case, agonist dose-response curves (10 data points each) are generated in the presence of selective antagonists using previously defined "blocking" concentrations (Thomas et al. (I), supra); μ receptors (1000 nM TIPP, 6 nM nor-BNI), δ receptors (2000 nM CTAP, 6 nM nor-BNI) and κ receptors (1000 nM TIPP, 2000 nM CTAP). Each curve is run with a 10 μM concentration of the standard agonist (DAMGO, U69,593 or SNC80). The data is expressed as a percent of the stimulation produced by the standard agonist. As described elsewhere (Thomas et al. (II), supra and Partilla et al., supra) compounds showing significant antagonist activity are further assessed with full dose-response curves to determine the functional $K_i$ values for inhibition of agonist-stimulated [35S]-GTP-γ-S binding using 10 μM DAMGO, 10 μM SNC80 or 10 μM U69,593.

Data Analysis. The data of the two separate experiments (opioid binding assays) or three experiments ([$^{35}$S]-GTP-γ-S assay) are pooled and fit, by using the nonlinear least-squares curve-fitting program MLAB-PC (Civilized Software, Bethesda, Md.) to the two-parameter logistic equation (Rodbard et al., Statistical Characterization of the Random Errors in the Radioimmunoassay Dose-Response Variable. *Clin. Chem.* 1976, 22, 350-358.) for the best-fit estimates of the IC$_{50}$ and slope factor. The $K_i$ values were then calculated using the equation: $K_i = IC_{50}/(1+[L]/K_d)$.

Bioassays in Smooth Muscle Preparations. The functional activity profiles of selected ligands are also determined in the mouse vas deferens (MVD) and guinea pig ileum (GPI) smooth muscle preparations as described previously. (See Kramer et al., In vitro Potency, Affinity and Agonist Efficacy of Highly Selective Delta Opioid Receptor Ligands. *J. Pharmacol. Exp. Ther.* 1993, 266, 577-584; and Porreca et al., Opioid Agonist Affinity in the Guinea-pig Ileum and Mouse Vas Deferens. *Eur. J. Pharmacol.* 1990, 179, 129-139.

The agonist activity is determined by the ability of the compound to inhibit electrically stimulated contractions of the GPI and MVD. The GPI is primarily a μ receptor preparation, even though the ileum does also contain κ receptors. In the MVD, the opioid effects are predominantly mediated through δ receptors, but μ and κ receptors also exist in this tissue. Testing for antagonist activity is carried out by preincubating the muscle preparations with the test compound 30 min prior to washing with buffer and testing with the standard δ agonist DPDPE in the MVD and the μ agonist PL-017 in the GPI. The antagonist and agonist potencies of the tested compounds are listed in Table 3.

Electrically induced smooth muscle contractions of mouse vas deferens and strips of guinea pig ileum longitudinal muscle myenteric plexus are used. Tissues came from male ICR mice weighing 25-40 g and male Hartley guinea pigs weighing 250-500 g. The tissues are tied to gold chain with suture silk, suspended in 20 mL baths containing 37° C. oxygenated (95% O$_2$, 5% CO$_2$) Krebs bicarbonate solution (magnesium free for the MVD), and allowed to equilibrate for 15 min. The tissues are then stretched to optimal length previously determined to be 1 g tension (0.5 g for MVD) and allowed to equilibrate for 15 min. The tissues are stimulated transmurally between platinum wire electrodes at 0.1 Hz, 0.4 ms pulses (2-ms pulses for MVD), and supramaximal voltage. An initial dose-response curve of DPDPE or PL-017 is constructed at the start of each assay to establish tissue effects, allowing each tissue to be used as its own control. Tissues not producing typical results are not used. Experimental compounds were added to the baths in 14-60 μL volumes. Succeeding doses of agonist are added cumulatively to the bath at 3 min intervals to produce a concentration-response curve. The tissues are then washed extensively with fresh buffer until the original contraction height is reestablished. Agonist effects of the compounds at 1 µM are measured as percent inhibition of contraction height 10 min after addition to the bath. Antagonist effects to DPDPE and PL-017 are assayed after incubation of the tissues with 1 µM concentration of the compound in the bath for 30 min. The tissues are then washed with fresh buffer for 30 min, and the agonist dose-response curve was repeated. Rightward shifts in the dose-response curves are calculated by dividing the antagonized dose-response curve $IC_{50}$ value by the unantagonized $IC_{50}$ value. $IC_{50}$ values represent the mean of two to four tissues. $IC_{50}$ estimates and their associated standard errors are determined by using a computerized nonlinear least-squares method. (MINSQ Least Squares Parameter Estimation, version 3.05; MicroMath Inc., 1999.)

Analgesic Testing and Assessment of Tolerance Development. The analgesic activity of selected ligands is tested in mice using the 55° C. tail-flick test as previously described. (See Wells et al., supra.) The test compounds are administered by the intracerbroventricular (icv) route. The analgesic effects of the compounds that are evaluated are given in Table 4. The $A_{50}$ values are calculated for compounds which produced full antinociceptive effects with minimal or no toxicity. For those compounds for which the $A_{50}$ values could not be calculated, the percentage antinociception at the given dose is listed in the table. To determine whether the analgesic activity of the tested compounds is mediated through opioid receptors, the blockade of antinociceptive activity by pretreatment with naloxone is carried out. The analgesic activity was considered as naloxone sensitive if greater than 80% reduction in the antinociceptive response is observed. Selected compounds are also tested for antinociception in mice pretreated with the µ selective antagonist β-FNA (19 nmol, icv, −24 h).

Antinociceptive Studies. Male ICR mice (Harlan) are used for all evaluations. Mice are housed in a temperature and humidity controlled vivarium on a 12:12 h light:dark cycle with unlimited access to food and water prior to the formal procedures. Graded doses of morphine or the test compounds are injected intracerebroventricularly (icv) under light ether anesthesia. (Wells et al., supra.) Morphine sulfate is dissolved in distilled water and injected in a volume of 5 µL. The dihydrochloride salt of 7h is dissolved in water and injected in a volume of 5 µL. All other compounds are dissolved in 100% DMSO and injected in a volume of 5 µL. Antinociceptive assays are performed at various times after injection.

Tail-Flick Assay. Naive mice are baselined in the 55° C. tail-flick test as previously described.(Wells et al., supra and Bilsky et al., Competitive and Noncompetitive NMDA Antagonists Block the Development of Antinociceptive Tolerance to Morphine, but Not to Selective µ or δ Opioid Agonists in Mice. *Pain* 1996, 68, 229-237.)

Doses of morphine or the test compound are injected icv, and antinociception is assessed at 10, 20, 30, 45, 60, 80, 120 and 180 min postinjection. Percent antinociception is calculated using the formula: % MPE (maximal possible effect) =100×(test−control)/(cutoff−control) where control is the predrug observation, test is the postdrug observation, and cutoff is the maximal length of stimulus allowed (10 s for 55° C. tail-flick). Antinociceptive $A_{50}$ values and 95% confidence intervals are determined using linear regression software (FlashCalc). Opioid activity of the test compounds are assessed by pretreating animals with naloxone (10 mg/kg ip, −10 min) followed by an icv injection of an approximate $A_{90}$ dose of test compound. If a compound does not produce a full agonist effect, then the dose that produced the greatest antinociceptive effect is used. Antinociception is assessed in the 55° C. tail-flick test at 10, 20 and 30 min. A positive response to a fixed dose of naloxone is indicated when greater than 80% reduction in the antinociceptive effect of the agonist is observed.

Tolerance Regimen. Mice are injected twice daily (8 a.m. and 8 p.m.) with an approximate $A_{90}$ dose of morphine or $A_{90}$ doses of 7h for 3 days. Antinociceptive dose-response curves in the tail-flick assay are generated on the morning of the fourth day using the procedures outlined above.

Chart 1

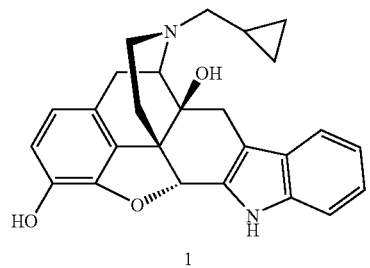

1

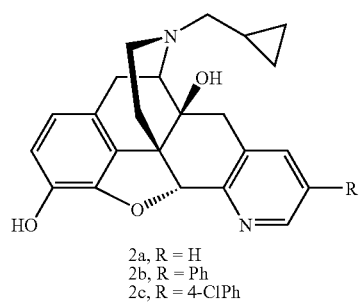

2a, R = H
2b, R = Ph
2c, R = 4-ClPh

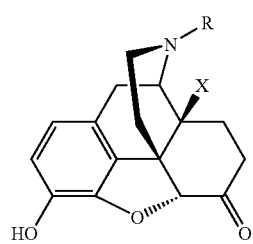

3, R = CPM, X = OH
4, R = Allyl, X = OH
5, R = Me, X = OH
6, R = Me, X = H

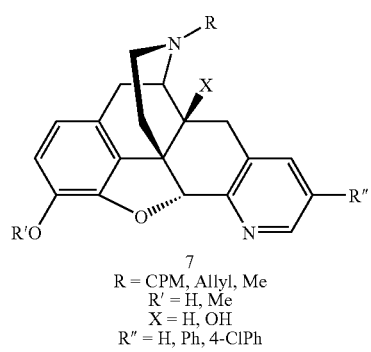

7
R = CPM, Allyl, Me
R' = H, Me
X = H, OH
R'' = H, Ph, 4-ClPh

TABLE 1

Binding affinities of the pyridomorphinans at the opioid δ, μ, and κ receptors in rodent brain membranes

| | | | | | $K_i$ (nM) ± SEM | | | selectivity ratio | |
|---|---|---|---|---|---|---|---|---|---|
| compd | R | X | R' | R" | $\delta^a$ | $\mu^b$ | $\kappa^c$ | μ/δ | κ/δ |
| 7a | Allyl | OH | H | 4-chlorophenyl | 8.2 ± 0.07 | 467 ± 19 | 75 ± 4.9 | 57 | 9 |
| 7b | Me | OH | H | H | 18 ± 1.4 | 7.9 ± 0.23 | 264 ± 18 | 0.4 | 15 |
| 7c | Me | OH | H | phenyl | 2.9 ± 0.12 | 26 ± 0.96 | 360 ± 17 | 9 | 124 |
| 7d | Me | OH | H | 4-chlorophenyl | 3.96 ± 0.23 | 230 ± 10 | 468 ± 17 | 58 | 118 |
| 7e | Me | OH | H | 4-bromophenyl | 4 ± 0.3 | 196 ± 4 | 432 ± 18 | 49 | 108 |
| 7f | Me | H | H | H | 8 ± 0.8 | 13 ± 0.5 | 66 ± 2 | 2 | 8 |
| 7g | Me | H | H | phenyl | 1.9 ± 0.09 | 24 ± 2 | 81 ± 5 | 13 | 43 |
| 7h | Me | H | H | 4-chlorophenyl | 4.4 ± 0.2 | 148 ± 9.5 | 78 ± 13 | 34 | 18 |
| 7i | Me | H | H | 4-bromophenyl | 5 ± 0.6 | 200 ± 11 | 91 ± 6 | 40 | 18 |
| 7j | Me | H | H | 3,4-dichlorophenyl | 3.7 ± 0.14 | 93 ± 4 | 278 ± 7 | 25 | 75 |
| 7k | Me | H | H | 2,4-dichlorophenyl | 1.1 ± 0.09 | 97 ± 4 | 403 ± 9 | 88 | 366 |
| 7l | CPM | H | H | 4-chlorophenyl | 2.6 ± 0.12 | 62 ± 3 | 6.0 ± 0.3 | 24 | 2.3 |
| 7m | Me | OH | Me | H | 143 ± 9 | 325 ± 16 | 6397 ± 353 | 2.2 | 45 |
| 7n | Me | OH | Me | phenyl | 34 ± 0.63 | 894 ± 19 | >10,000 | 26 | >294 |
| 7o | Me | OH | Me | 4-chlorophenyl | 21 ± 2 | 2052 ± 95 | >7100 | 98 | >338 |
| 7p | Me | OH | Me | 4-bromophenyl | 23 ± 1.3 | 1887 ± 72 | 7366 ± 522 | 82 | 320 |
| 7q | CPM | H | Me | 4-chlorophenyl | 41 ± 3 | 1974 ± 50 | 539 ± 20 | 48 | 13 |
| 2a[d] | CPM | OH | H | H | 0.78 ± 0.06 | 1.5 ± 0.09 | 8.8 ± 0.69 | 1.9 | 11 |
| 2b[d] | CPM | OH | H | phenyl | 0.87 ± 0.07 | 13.5 ± 1.0 | 17.6 ± 1.6 | 16 | 20 |
| 2c[d] | CPM | OH | H | 4-chlorophenyl | 2.2 ± 0.16 | 51.0 ± 8.0 | 20.0 ± 1.04 | 23 | 9.1 |

[a] Displacement of [³H]DADLE (1.3-2.0 nM) in rat brain membranes using 100 nM DAMGO to block binding to □ sites.
[b] Displacement of [³H]DAMGO (1.4-3.0 nM) in rat brain membranes.
[c] Displacement of [³H]U69,593 (1.2-2.2 nM) in guinea pig brain membranes.
[d] Data from Ananthan et al. (I).

TABLE 2

Antagonist and agonist functional activity of selected compounds in [³⁵S]GTP-γ-S binding assays in guinea pig caudate membranes

| | antagonist activity apparent $K_i$ (nM ± SD) | | | agonist activity $EC_{50}$ (nM ± SD) Emax % | | |
|---|---|---|---|---|---|---|
| compd | $\delta^a$ | $\mu^b$ | $\kappa^c$ | $\delta^d$ | $\mu^e$ | $\kappa^f$ |
| 7b | >1000 | >1000 | >1000 | g | 2999 ± 672 40 ± 2% | g |
| 7c | 920 ± 240[h] | >1000 | >1000 | g | 658 ± 185 27 ± 2% | g |
| 7d | 17 ± 2.6 | >1000 | 767 ± 54 | g | g | g |
| 7f | 595 ± 48 | >1000 | >1000 | g | 502 ± 76 44 ± 1% | g |
| 7g | >1000 | >1000 | >1000 | g | 1031 ± 104 60 ± 1% | g |
| 7h | 10.95 ± 1.0 | i | 333 ± 25 | g | 902 ± 170 48 ± 2% | g |
| 7i | 55 ± 16[h] | >1000 | 265 ± 29 | g | 3216 ± 573 59 ± 3% | g |
| 7j | 74 ± 14[h] | >1000 | 4770 ± 1500[h] | g | 1313 ± 236 63 ± 3% | g |
| 7k | 1.08 ± 0.11 | >1000 | 308 ± 21 | g | 225 ± 31 51 ± 5% | g |
| 7l | 1.56 ± 0.14 | 9.2 ± 0.86 | 11.23 ± 0.62 | g | g | g |
| 2c | 0.184 ± 0.011 | 7.8 ± 0.42 | 11.18 ± 0.44 | g | g | g |
| 1, NTI | 0.062 ± 0.006 | 3.21 ± 0.20 | 8.85 ± 0.8 | g | g | g |
| SNC80 | na[j] | na | na | 758 ± 131 100% | na | na |
| DAMGO | na | na | na | na | 414 ± 47 100% | na |

TABLE 2-continued

Antagonist and agonist functional activity of selected compounds in [$^{35}$S]GTP-γ-S binding assays in guinea pig caudate membranes

| compd | antagonist activity apparent $K_i$ (nM ± SD) | | | agonist activity $EC_{50}$ (nM ± SD) Emax % | | |
|---|---|---|---|---|---|---|
| | δ[a] | μ[b] | κ[c] | δ[d] | μ[e] | κ[f] |
| Morphine | na | na | na | g | 288 ± 80 32 ± 2% | g |
| U69593 | na | na | na | na | na | 377 ± 39 100% |

[a]SNC-80 (10 μM) was used as the agonist selective for the δ receptor.
[b]DAMGO (10 μM) was used as the agonist selective for the μ receptor.
[c]U69,593 (10 μM) was used as the agonist selective for the κ receptor.
[d]The μ and κ sites were blocked with the antagonists CTAP (2 μM) and nor-BNI (6 nM).
[e]The δ and κ sites were blocked with the antagonists TIPP (1 μM) and nor-BNI (6 nM).
[f]The δ and μ sites were blocked with TIPP (1 μM) and CTAP (2 μM).
[g]Not active as an agonist. [h] $IC_{50}$ values; $K_i$ values could not be calculated due to partial inhibition of agonist stimulated [$^{35}$S]GTP-γ-S binding.
[i]$K_i$ value could not be calculated due to agonist activity.
[j]na = not applicable.

TABLE 3

Antagonist and agonist functional activity of selected compound in mouse vas deferens (MVD) and guinea pig ileum (GPI) smooth muscle assays

| | antagonist activity | | agonist activity | |
|---|---|---|---|---|
| compd | MVD (δ) $K_e$ (nM)[a] | GPI (μ) $K_e$ (nM)[b] | MVD (δ) $IC_{50}$ (nM) or % max resp[c] | GPI (μ) $IC_{50}$ (nM) or % max resp[c] |
| 7b | d | d | 49% | 523.1 ± 94.8 |
| 7c | d | d | 212.7 ± 55.8 | 211.2 ± 35.9 |
| 7d | 38.17 ± 14.68 | d | 58% | 8.7% |
| 7f | d | d | 151.9 ± 25.5 | 67.65 ± 10.1 |
| 7g | d | d | 48.43 ± 8.65 | 98.7 ± 20.1 |
| 7h | 21.9 ± 2.14 | d | 565.2 ± 12.7 | 177.2 ± 41.5 |
| 7i | 20.0 ± 6.59 | d | 44% | 665.9 ± 126.9 |
| 7j | d | d | 489.3 ± 164.5 | 446.9 ± 162.8 |
| 7k | 5.02 ± 1.56 | d | 28.3% | 723.7 ± 131.5 |
| 7l | 6.00 ± 1.33 | d | 7.9% | 108.7 ± 27.2 |
| 2a[e] | 37.0 ± 1.0 | 190 ± 65 | 0% | 0% |
| 2b[e] | 3.7 ± 1.0 | 43 ± 6.6 | 4.7% | 0% |
| 2c[e] | 0.91 ± 0.48 | d | 21% | 163 ± 22 |

[a]Determined using DPDPE as the agonist ligand for the δ receptor.
[b]Determined using PL-017 as the agonist ligand for the μ receptor.
[c]Partial agonist activity is expressed as the percentage inhibition of contraction at a concentration of 1 μM.
[d]The agonist effects precluded the determination of antagonist effects.
[e]Data from Ananthan et al.(1).

TABLE 4

Analgesic activity of selected ligands in the mouse tail-flick assay[a]

| compd | $A_{50}$ or % nociception | 95% confidence limits | naloxone sensitivity[b] |
|---|---|---|---|
| 7b | 67.1 nmol | 49.0-91.8 nmol | yes |
| 7c | 64% @ 100 nmol | c | no |
| 7d | 43% @ 300 nmol | c | partial |
| 7f | 75% @100 nmol | c | no |
| 7g | 48% @ 100 nmol | c | yes |
| 7h | 42.8 nmol | 30.6-59.8 nmol | yes |
| 7i | 47.2 nmol | 31.3-71.2 nmol | yes |
| 7j | 44% @ 300 nmol | c | ND[d] |
| 7k | 40% @ 60 nmol[e] | c | ND |
| 7l | 18% @ 300 nmol | c | ND |
| 2c | 21% @ 100 nmol[f] | c | yes |
| morphine | 4.2 nmol | 3.0-6.9 nmol | yes |

[a]Compounds were administered icv with $A_{50}$ values calculated at time of peak drug effect.
[b]Compounds exhibiting greater than 80% reduction in the antinociceptive effect to a fixed does of naloxone are designated "yes" for naloxone sensitivity.
[c]95% confidence levels could not be calculated.
[d]ND = not determined.
[e]Doses of 100-600 nmol produced less than 40% MPE.
[f]Doses of 300 and 600 nmol produced less than 10% MPE.

RESULTS FROM TEST

An examination of the affinities of the target compounds 7a-l reveals that, with the exception of 7b, all of the ligands display high affinity binding at the δ site with $K_i$ values <10 nM and are δ selective, their binding potencies at δ site being higher than their affinities at the μ and κ sites. Compounds 7b and 7f possess the basic morphinan unit present in oxymorphone and hydromorphone, respectively and do not carry any substituent on the fused pyridine ring system. These two compounds display a relatively non-selective binding profile between μ and δ receptors ($K_i$ μ/$K_i$ δ=0.4 for 7b, $K_i$ μ/$K_i$ δ=2.0 for 7f). Their affinities at the κ site are significantly lower than their affinities at δ and μ sites. The introduction of phenyl group at the 5'-position on these two templates gives compounds 7c and 7g, which display 4- to 6-fold enhanced affinity at the δ site in comparison to the parent compounds. This improvement in the binding affinity of the phenyl-substituted analogues at the δ site is accompanied by a decrease in affinity at μ and κ sites, thus leading to an enhancement in δ selectivity profile of these compounds. Thus it appears that aryl groups placed at the 5'-position of the pyridomorphinan templates encounters favorable interactions at the binding site of the δ receptor as opposed to unfavorable interactions at the μ and κ receptors. Introduction of chlorine or bromine substituent at the p-position of the free-rotating phenyl ring in 7c or 7g brings about a modest decrease in binding affinity at the δ site. Of the two isomeric dichlorophenyl compounds 7j and 7k, the 2,4-dichlorophenyl compound 7k binds with higher affinity at the δ site than the 3,4-dichlorophenyl compound. Among phenolic compounds 7a-l, the 2,4-dichlorophenyl compound 7k displays the highest δ receptor binding affinity ($K_i$=1.1 nM) and highest δ receptor binding selectivity with μ/δ and κ/δ selectivity ratios of 88 and 366, respectively.

A comparison of the affinities of compounds possessing N-CPM group (2a-c) with those possessing an N-methyl group (7b-d) indicates that replacing the CPM group with methyl group in general leads to reduction in affinities at all three receptors. The reduction in affinities at the κ sites are relatively larger than the reductions in binding affinities at δ or μ sites. Compared to the N-CPM compound 2c, the N-allyl analogue 7a also displays reduced affinities at the δ, μ, and κ receptors with greater reduction in affinity at the μ site (9-fold) than at δ (4-fold) or κ sites (4-fold). Comparison of the affinities of 7b-e with 7f-h and those of 2c with 7l indicates that the replacement of the 14-hydroxyl group with a hydrogen atom brings about a modest change in the affinity at the δ and μ sites (less than 3-fold change in affinity). At the κ site, however, the deoxy compounds display 3- to 6-fold higher affinity than their 14-hydroxy counterparts. The presence of a free phenolic hydroxyl group is usually considered essential for high affinity binding at opioid receptors. The affinities of the phenolic methyl ethers are typically lower than their corresponding phenolic compounds at all three bonding sites. The magnitude of reduction in affinity at the δ site is much less (5- to 16-fold) than the reduction in affinity at the μ (8- to 41-fold) or κ sites (17- to >300-fold).

As shown by the functional activity data in the [$^{35}$S]GTP-γ-S assays (Table 2), most of the compounds examined in the present invention that were tested, in general displayed the desired profile of μ agonist/δ antagonist activity. In the antagonist assays at the δ receptors, compounds 7c, 7i, and 7j lack any agonist effect at δ receptors, but fail to inhibit SNC-80 stimulated binding of [$^{35}$S]GTP-γ-S to 100% with increasing concentrations of these ligands. The maximum percentage inhibition displayed by 7c, 7i, and 7j are 61±3%, 69±3%, and 58±3%, respectively. A similar partial inhibition profile (maximum inhibition 66±6%) is also observed for 7j at the κ receptors, which also lack κ agonist activity. The partial inhibition profile displayed by these ligands is exemplified by the concentration-response curve for 7j shown in FIG. 1. For these compounds, the calculated $IC_{50}$ values instead of $K_i$ values are listed in Table 2.

Among the compounds tested, only two compounds, 7d and 7l failed to display agonist activity at the μ receptor. Compound 7l is the 14-deoxy analogue of 2c and carries the N-CPM group at the 17-position. Although all other ligands carrying an N-methyl group display μ agonist activity with varying potencies, this is not true for 7d, however, because of its low binding affinity at the μ receptor. Among the ligands that displayed μ agonist activity, compound 7k is the most potent with an $EC_{50}$ value of 225 nM which is comparable to the $EC_{50}$ values of morphine (288 nM) and DAMGO (414 nM). The rank order of potencies for the agonist ligands were: 7k>7f>7c>7h>7g>7j>7b>7i, and there appears to be no strict correlation between the agonist potency and the binding potency of these ligands at the μ receptor. The agonist efficacies of these ligands, as indicated by their percentage maximum stimulation (Emax) values, are in the range of 27% (7c) to 60% (7g). With the exception of 7c, all of these ligands are more efficacious than morphine (Emax=32%) but less efficacious than DAMGO (Emax=100%). With regard to antagonist activity, the N-CPM compound 7l displays significant antagonist potency at all three receptors. All of the N-methyl compounds examined display no or only weak antagonist activity at the μ and κ receptors. Interestingly, however, most of the compounds display moderate antagonist potencies at the δ receptor. The pyridomorphinans 7d and 7h possessing the 4-chlorophenyl substituent are N-methyl analogues of the N-CPM compound 2c. These two compounds 7d and 7h display δ antagonist $K_e$ values of 17 nM and 10.95 nM, respectively as compared to the $K_e$ value of 0.184 nM for 2c. Thus, the exchange of N-CPM group with a methyl group brings about a significant reduction in the δ antagonist potency, but without altering the intrinsic antagonist profile of these ligands at the δ receptor. Interestingly, while the introduction of a second chlorine atom at the m-position of the chlorophenyl ring of 7h (compound 7j) did not significantly change the binding affinity or the antagonist potency at the δ receptor, the introduction of the chlorine atom at the o-position (compound 7k) provided a 4-fold enhancement in binding affinity and a 10-fold improvement in antagonist potency at the δ receptor. Among the ligands studied, the 2,4-dichlorophenyl compound 7k is not only the most potent δ antagonist but also the most potent μ agonist, thus making it the best mixed μ agonist/δ antagonist ligand in vitro. The profile of 7h is similar to that of 7k but with somewhat weaker antagonist and agonist potencies at the δ and μ receptors, respectively, in vitro. Some δ antagonists (7b, 7e, 7f, 7g) display a marked discrepancy between the binding $K_i$ values (Table 1) and the corresponding functional $K_i$ values (Table 2).

The functional activity results obtained for the selected compounds in the smooth muscle assays (Table 3) are somewhat similar to that obtained in the [$^{35}$S]GTP-γ-S assays. All of the ligands that display agonist activity in the [$^{35}$S]GTP-γ-S assays at the μ site also display agonist activity in the GPI. One significant exception is the activity of 7l, which is a potent agonist in the GPI ($IC_{50}$=108 nM) but is found to be an antagonist at the μ site in the [$^{35}$S]GTP-γ-S assays. While none of the compounds display any significant agonist activity at the δ site in the [$^{35}$S]GTP-γ-S assays, a few compounds, 7c, 7f, 7g, 7h, and 7j display agonist activity in the MVD smooth muscle preparations. It appears that the agonist activity displayed by these compounds in the MVD may be due to their agonist effects at the μ receptors. In one instance studied, it has been found that the agonist activity of 7f in the MVD is blocked by the nonselective antagonist naloxone but not by the δ selective antagonist ICI-174,864. Among the compounds studied, δ antagonist $K_e$ values could be determined for 7d, 7h, 7i, 7k, and 7l in the MVD. The antagonist $K_e$ values for these compounds are in the range of 5 nM (7k) to 38 nM (7d). Compounds 7h and 7k were the two compounds that displayed in vitro μ agonist/δ antagonist profile of activity in both the [$^{35}$S]GTP-γ-S and the smooth muscle assay systems.

The structure-activity relationships observed, suggest that fusion of a pyridine ring at the 6,7-position of 4,5-epoxymorphinans has the effect of increasing the binding affinity at the δ receptor and decreasing the binding affinity at the μ receptor, thus leading to templates that are nearly equipotent in binding at the δ and μ receptors. These pyridomorphinans appear to have a basic tendency to interact with δ receptors as antagonists irrespective of the nature of the alkyl substituent (CPM or methyl) on the morphinan nitrogen. Their functional activity at the μ receptor, however, appears to be governed by the nature of the N-alkyl substituent, those with the CPM group interacting as antagonists and those with N-methyl group interacting as agonists. Further modulations in binding and functional activity of the pyridomorphinans could be achieved through introduction of appropriate substituents, particularly at the 5'-position of the pyridine ring.

Figure 2:
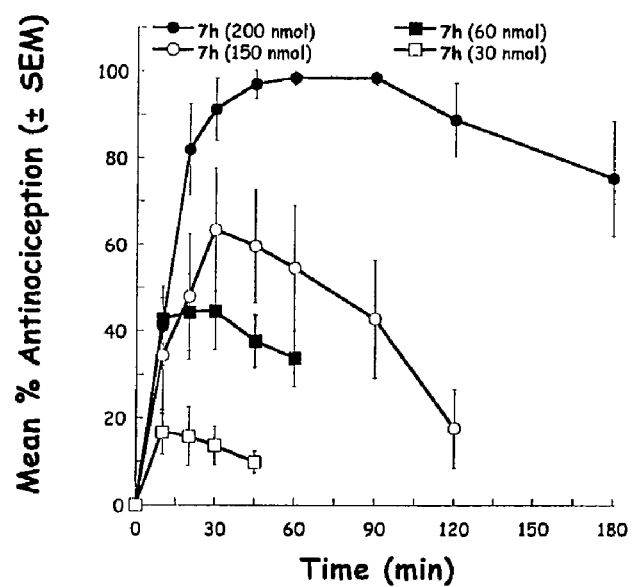
FIG. 2 illustrates an Antinociceptive dose- and time-response curves for 7h (chart 1)(icv) in the 55° C. tail-flick test.
Figure 3:
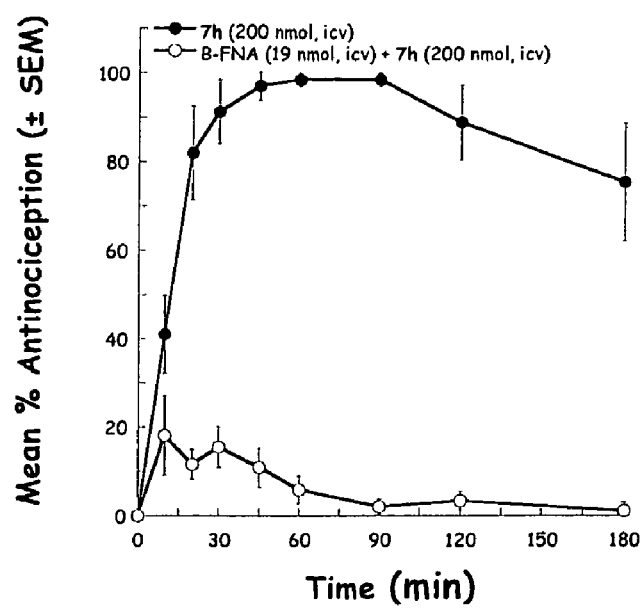
FIG. 3 illustrates an Antinociceptive dose- and time-response curve for 7h (chart 1)(icv) with and without pretreatment with β-FNA (19 nmol, icv, −24 h).
Figure 4:
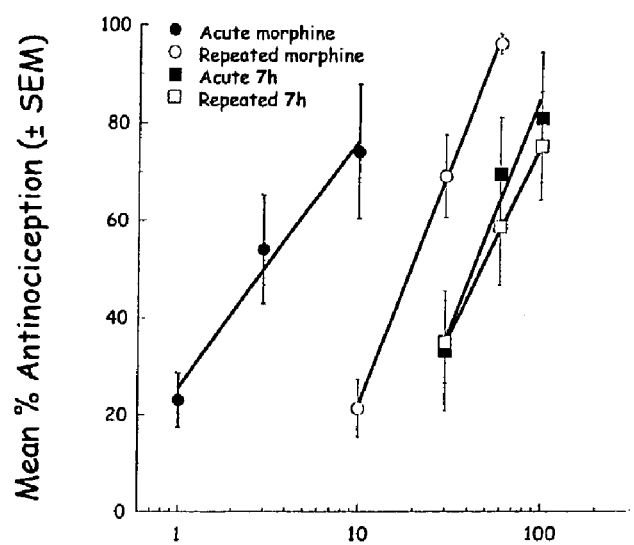
FIG. 4 illustrates an Antinociceptive dose-response curves for naive control mice and mice injected repeatedly with $A_{90}$ doses of icv morphine or 7h (chart 1) given twice daily for 3 days.

All of the compounds that are evaluated in the functional assays in vitro are evaluated for antinociceptive activity in mice using the tail flick assay (Table 4). Among the compounds tested, the antinociceptive $A_{50}$ values could be determined for only three compounds, 7b, 7h, and 7i. Factors that prevented determining the $A_{50}$ values for the other compounds include: lack of efficacy (7c, 7j, 7k, and 7l), lack of potency (7d), insensitivity to naloxone (7f), and toxicity (7g). All of the compounds examined in the present invention were found to be more efficacious in the tail-flick assay than the previously disclosed compound 2c. From in vitro functional evaluations, compounds 7k and 7h are identified as ligands of interest as mixed μ agonist/δ antagonist. Of these two ligands, the δ antagonist/μ agonist profile of 7k is superior to that of 7h in vitro. In the antinociceptive evaluations, however, compound 7k is found to be not as efficacious as 7h. Compound 7h displays full agonist efficacy with an $A_{50}$ potency value of 21.9 nM in the tail flick assay in mice (FIG. 2). The antinociceptive activity of this compound is completely blocked by the μ selective antagonist β-FNA (FIG. 3) confirming that the analgesic activity of this compound is indeed mediated through opioid μ receptors. From these tests, the pyridomorphinan 7h emerges as a ligand possessing mixed μ agonist/δ antagonist activity in vitro and in vivo. This compound when tested in the tolerance development assays involving repeated injections of the compound for three days induces an insignificant shift in the antinociceptive potency (less than 1.1-fold increase in $A_{50}$ value) indicating very little development of tolerance. This is in contrast to morphine, which in the same paradigm, produced a significant 6.4-fold shift in the $A_{50}$ values indicating the development of tolerance to its analgesic effects (FIG. 4). The lack of tolerance displayed by this nonpeptide μ agonist/δ antagonist ligand 7h supports the hypothesis that ligands with a mixed μ agonist/δ antagonist profile of activity have the potential of becoming therapeutically useful analgesic agents devoid of tolerance and dependence development commonly associated with pure μ agonist analgesics such as morphine.

The fusion of a pyridine ring on the oxymorphone and hydromorphone framework gives pyridomorphinans that bind with nearly equal affinity to μ and δ receptors, and with much less affinity at the κ receptors. Introduction of aryl substituents at the 5'-position on these pyridomorphinan scaffolds in general improve the affinity and antagonist potency at the δ receptor with retention of agonist activity at the μ receptors, thus leading to mixed μ agonist/δ antagonist ligands. Antinociceptive evaluations with 7h by the tail-flick test in mice demonstrates that the compound produces antinociceptive effects without inducing analgesic tolerance on repeated administration.

The pharmaceutically acceptable effective dosage of the active compound of the present invention to be administered is dependent on the species of the warm-blooded animal (mammal), the body weight, age and individual condition, and on the form of administration.

The pharmaceutical composition may be oral, parenateral, suppository or other form which delivers the compounds used in the present invention into the bloodstream of a mammal to be treated.

The compounds of the present invention can be administered by any conventional means available for use in conjunction with pharmaceutical, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desired. A daily dosage of active ingredient can be expected to be about 0.001 to 1000 milligram (mg) per kilogram (kg) of body weight, with the more typical dose being 0.1 to about 30 mg/kg.

Dosage forms (compositions suitable for administration) typically contain from about 1 mg to about 100 mg of active ingredient per unit. In these pharmaceutical compositions, the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. The active ingredient can also be administered intranasally (nose drops) or by inhalation. Other dosage forms are potentially possible such as administration transdermally, via a patch mechanism or ointment.

Gelatin capsules contain the active ingredient and powdered carriers, such as lactose, starch, cellulose.

Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.9 mg of lactose. Appropriate coatings may be applied to increase palatability or delay absorption.

The foregoing disclosure includes all the information deemed essential to enable those skilled in the art to practice the claimed invention.

The foregoing description of the invention illustrates and describes only the preferred embodiments of the present invention. However, as mentioned above, it is to be understood that the invention is capable of being made and used in various other combinations, modifications, and environments, and is capable of being changed or modified within the scope of the inventive concept as expressed herein, commensurate with the above teachings and/or the skill or knowledge of persons skilled in the relevant art. The embodiments described hereinabove are further intended to explain the best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

All publications and patent applications cited in this specification are herein incorporated by reference as if each individual publication or patent application were specifically and individually indicated to be incorporated by reference.

What is claimed is:

1. A compound represented by the Formula:

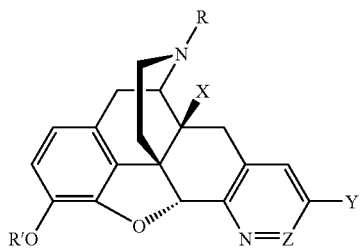

Wherein R is selected from the group consisting of $C_{1-6}$ alkyl; $C_{4-6}$ cycloalkylalkyl; and $C_{3-6}$ alkenyl;
R' is H or $C_{1-6}$ alkyl;
X is H or OH;
Y is selected from the group consisting of alkyl, cycloalkyl, aryl, heteroaryl, arylalkyl and aroyl; and
Z is CH or N; provided that when Z is CH and R is $C_{4-6}$ cycloalkylalkyl or $C_{3-6}$ alkenyl, then X is H; and pharmaceutically acceptable salts thereof.

2. The compound of claim 1 wherein R is a $C_{1-6}$ alkyl group.

3. The compound of claim 1 wherein R is methyl.

4. The compound of claim 3 wherein X is H.

5. The compound of claim 1 wherein X is H.

6. The compound of claim 1 wherein Y is aryl.

7. The compound of claim 1 being selected from the group consisting of:
6,7-Didehydro-3,14-dihydroxy-4,5α-epoxy-7-methylpyrido[2',3':6,7]morphinan;
6,7-Didehydro-4,5α-epoxy-14-hydroxy-3-methoxy-17-methylpyrido[2',3':6,7]morphinan;
6,7-Didehydro-3,14-dihydroxy-4,5α-epoxy-17-methyl-5'-phenylpyrido[2',3':6,7]morphinan;
6,7-Didehydro-14-hydroxy-4,5α-epoxy-3-methoxyl-17-methyl-5'-phenylpyrido[2',3':6,7]morphinan;
5'-(4-Chlorophenyl)-6,7-didehydro-3,14-dihydroxy-4,5α-epoxy-17-methylpyrido[2',3':6,7]morphinan;
5'-(4-Chlorophenyl)-6,7-didehydro-14-hydroxy-4,5α-epoxy-3-methoxyl-17-methylpyrido[2',3':6,7]morphinan;
5'-(4-Bromophenyl)-6,7-didehydro-3,14-dihydroxy-4,5α-epoxy-17-methylpyrido[2',3':6,7]morphinan;
5'-(4-Bromophenyl)-6,7-didehydro-3,14-dihydroxy-4,5α-epoxy-3-methoxy-17-methylpyrido[2',3':6,7]morphinan;
6,7-Didehydro-4,5α-epoxy-3-hydroxy-17-methylpyrido[2',3':6,7]morphinan;
6,7-Didehydro-4,5α-epoxy-3-hydroxy-17-methyl-5'-phenylpyrido[2',3':6,7]morphinan;
5'-(4-Chlorophenyl)-6,7-didehydro-4,5α-epoxy-3-hydroxy-17-methylpyrido[2',3':6,7]morphinan;
5'-(4-Bromophenyl)-6,7-didehydro-4,5α-epoxy-3-hydroxy-17-methylpyrido[2',3':6,7]morphinan;
5'-(3,4-Dichlorophenyl)-6,7-didehydro-4,5α-epoxy-3-hydroxy-17-methylpyrido[2',3':6,7]morphinan;
5'-(2,4-Dichlorophenyl)-6,7-didehydro-4,5α-epoxy-3-hydroxy-17-methylpyrido[2',3':6,7]morphinan;
5'-(4-Chlorophenyl)-17-(cyclopropylmethyl)-6,7-didehydro-4,5α-epoxy-3-hydroxypyrido[2',3':6,7]morphinan;
5'-(4-Chlorophenyl)-17-(cyclopropylmethyl)-6,7-didehydro-4,5α-epoxy-3-methoxypyrido[2',3':6,7]morphinan;
5'-(4-Chlorophenyl)-17-[(2-cyclohexyl)ethyl]-6,7-didehydro-4,5α-epoxy-3-methoxypyrido[2',3':6,7]morphinan;
5'-(4-Chlorophenyl)-17-[(2-cyclohexyl)ethyl]-6,7-didehydro-4,5α-epoxy-3-hydroxypyrido[2',3':6,7]morphinan;
5'-(Cyclohexyl)-17-(cyclopropylmethyl)-6,7-didehydro-3,14-dihydroxy-4,5α-epoxypyrido[2',3':6,7]morphinan;
5'-(Cyclohexyl)-6-7-didehydro-4,5α-epoxy-3-hydroxy-17-methylpyrido[2',3':6,7]morphinan;
5'-Benzyl-6,7-didehydro-3,14-dihydroxy-4,5α-epoxy-17-methylpyrido[2',3':6,7]morphinan;
6,7-Didehydro-4,5α-epoxy-3-hydroxy-5'-(2-hydroxybenzoyl)-17-methylpyrido[2',3':6,7]morphinan;
17-(Cyclopropylmethyl)-6,7-didehydro-3,14-dihydroxy-4,5α-epoxy-6'-phenylpyridazino[3',4':6,7]morphinan;
17-(Cyclopropylmethyl)-6,7-didehydro-3,14-dihydroxy-4,5α-epoxy-6'-(4-chlorophenyl)pyridazino[3',4':6,7]morphinan;
6,7-Didehydro-4,5α-epoxy-3-hydroxy-17-methyl-6'-phenylpyridazino[3',4':6,7]morphinan; and
6,7-Didehydro-4,5α-epoxy-3-hydroxy-17-methyl-6'-(4-chlorophenyl)pyridazino[3',4':6,7]morphinan.

8. The compound of claim 1 being 5'-(4chlorophenyl)-6,7-didehydro-3,14-dihydroxy-4,5α-epoxy-17methylpyrido[2',3':6,7]morphinan.

9. A method for treating a patient suffering from pain which comprises administering to the patient an effective amount of at least one compound according the claim 1.

10. A method for treating a patient suffering from cocaine or methamphetamine abuse which comprises administering to the patient an effective amount of at least one compound according the claim 1.

11. A method for treating a patient suffering from dependence on or tolerance to morphine which comprises administering to the patient at least one of the compounds of claim 1 in an amount effective to modulate the tolerance to or dependence on morphine.

12. A method for treating a patient suffering from pain which comprises administering to the patient a pain treating effective amount of at least one compound according the claim 2.

13. A method for treating a patient suffering from pain which comprises administering to the patient a pain treating effective amount of at least one compound according the claim 3.

14. A method for treating a patient suffering from pain which comprises administering to the patient a pain treating effective amount of at least one compound according the claim 4.

15. A method for treating a patient suffering from pain which comprises administering to the patient a pain treating effective amount of at least one compound according the claim 5.

16. A method for treating a patient suffering from pain which comprises administering to the patient a pain treating effective amount of at least one compound according the claim 6.

17. A method for treating a patient suffering from pain which comprises administering to the patient a pain treating effective amount of at least one compound according the claim 7.

18. A method for treating a patient suffering from pain which comprises administering to the patient a pain treating effective amount of at least one compound according the claim 8.

19. A method for treating a patient suffering from cocaine or methamphetamine abuse which comprises administering to the patient an effective amount of at least one compound according the claim 7.

* * * * *